US005614620A

United States Patent [19]
Liao et al.

[11] Patent Number: 5,614,620
[45] Date of Patent: Mar. 25, 1997

[54] DNA BINDING PROTEINS INCLUDING ANDROGEN RECEPTOR

[75] Inventors: Shutsung Liao; Chawnshang Chang, both of Chicago, Ill.

[73] Assignee: Arch Development Corporation, Chicago, Ill.

[21] Appl. No.: 149,691

[22] Filed: Nov. 8, 1993

Related U.S. Application Data

[63] Continuation of Ser. No. 438,775, Nov. 17, 1989, abandoned, which is a continuation-in-part of Ser. No. 312,763, Feb. 21, 1989, abandoned, which is a continuation-in-part of Ser. No. 253,807, Oct. 5, 1988, abandoned, which is a continuation-in-part of Ser. No. 176,107, Mar. 30, 1988, abandoned.

[51] Int. Cl.$^6$ .......................... C07H 21/04; C12N 15/00; C12N 1/20
[52] U.S. Cl. .................... 536/23.5; 435/252.33; 435/320.1; 435/172.3; 435/325; 536/23.1; 935/11; 935/24; 935/29; 935/73
[58] Field of Search ............................ 536/23.1, 23.5; 435/69.1, 172.3, 240.2, 252.33, 320.1; 935/11, 17

[56] References Cited

U.S. PATENT DOCUMENTS

| | | |
|---|---|---|
| 4,683,195 | 7/1987 | Mullis . |
| 4,683,202 | 7/1987 | Mullis . |
| 4,800,159 | 1/1989 | Mullis . |

FOREIGN PATENT DOCUMENTS

| | | |
|---|---|---|
| WO89/09223 | 10/1989 | WIPO . |
| WO89/09791 | 10/1989 | WIPO . |

OTHER PUBLICATIONS

Amrhein, J.A., et al., Proc. Nat. Acad. Sci. USA, 73:891–894 (1976).
Arriza, J.L., et al., Science, 237:268–275 (1987).
Benbrook, D., et al., Science, 238:788–791 (1987).
Chang, C., et al., The Journal of Biological Chemistry, 262:11901–11903 (1987).
Chang, C., et al., The Journal of Biological Chemistry, 262:2826–2831 (1987).
Conneely, O.M., et al., Science, 233:767–770 (1986).
Danielsen, M., et al., EMBO J., 5:2513–2522 (1986).
Giguere, V., et al., Nature, 331:91–94 (1988).
Giguere, V., et al., Nature, 330:624–629 (1987).
Gorman, C., pp. 143–190 in "DNA Cloning", vol. 2, D.M. Glover, ed. Chapter 6.
Gorski, J., et al., Ann. Rev. Physiol., 42:425–450 (1976).
Govindan, M.V., et al., J. Endocrinol. Invest., 10 (Suppl. 2) (1987). [Abstract].
Green, S., et al., Nature, 320:134–139 (1986).
Greene, G.L., et al., Science, 231:1150–1154 (1986).
Hollenberg, S.M., et al., Nature, 318:635–641 (1985).
Jensen, E.V., et al., Proc. Nat'l Acad. Sci. (USA), 59:632–638 (1968).
Kozak, M., Nature, 308:241–246 (1984).

Krust, A., et al., The EMBO Journal, 5:891–897 (1986).
Kunkel, I.M., et al., Nucleic Acids Research, 11:7961 (1983).
Law, M.L., et al., Proc. Nat'l. Acad. Sci. USA, 84:2877–2881 (1987).
Liao, S., et al., pp. 633–680 in Biochemistry of Steroid Hormones, Second edition, H.L.J. Makin, ed. (Blackwell Sci. Publ. Oxford, (1984).
Liao, et al., Proc. Nat'l. Acad. Sci. USA, 82:8345–8348 (1985).
Liao, et al., J. Steroid Biochem., 20:11–17 (1984).
Liao, et al., The Journal of Biological Chemistry, 248:6154–6162 (1973).
Loosfelt, H., et al., Proc. Nat'l. Acad. Sci. USA, 83:9045–9049 (1986).
Lyon, M.F., et al., Nature, 227:1217–1219 (1970).
McDonnell, D.P., et al., Science, 235:1214–1217 (1987).
Meyer, W.J., et al., Proc. Nat'l. Acad. Sci. USA, 72:1469–1472 (1975).
Miesfeld, R., et al., Cell, 46:389–399 (1986).
Misrahi, M., et al., Biochemical and Biophysical Research Communications, 143:740–748 (1987).
Neri, R.O., et al., Invest. Urol., 10:123–130 (1972).
Ringold, G.M., Ann. Rev. Pharmacol. Toxicol, 25:529–566 (1985).
Saltzman, A.G., et al., The Journal of Biological Chemistry, 262:432–437 (1987).
Sap, J., et al., Nature, 324:635–640 (1986).
Schilling, K., et al., The Prostate, 5:581–588 (1984).
Weinberger, C., et al., Nature, 324:641–646 (1986).
Weinberger, C., et al., Nature, 318:670–672 (1985).
Yamamoto, K.R., Ann. Rev. Genet., 19:209–252 (1985).
Chang, C., et al., Proc. Nat'l. Acad. Sci. USA, 85:7211–7215 (Oct. 1988).
Chang, C., et al., Science, 240:324–326 (1988).
Dieckmann, C.L., et al., The Journal of Biological Chemistry, 260:1513–1520 (1985).
Engvall, E., et al., Biochimica et Biophysica Acta, 251:427–434 (1971).
Evans, R.M., Science, 240:889–895 (1988).
Kozbor, D., et al., Eur. J. Immunol., 14:23–27 (1984).
Saiki, R.K., et al., Science, 230:1350–1354 (1985).
Young, C.Y.F., et al., Endocrinology, 123:601–610 (1988).
Govindan, et al., Progress in Cancer Research and Therapy, Raven Press (New York, USA) vol. 35, pp. 49–54.

(List continued on next page.)

*Primary Examiner*—Jasemine C. Chambers
*Attorney, Agent, or Firm*—Arnold, White & Durkee

[57] ABSTRACT

Disclosed are DNA sequences encoding DNA binding polypeptides including androgen receptor (AR) and TR2 polypeptides. Illustratively, human and rat AR-cDNA have 79 kD and 98 kD polypeptide expression products which are immunoprecipitable by human auto-immune anti-androgen receptor antibodies and are capable of binding androgens specifically and with high affinity. Also disclosed are antibodies and immunological methods and materials for detection of androgen receptor and TR2 polypeptides and hybridization methods and materials for detection of AR-and TR2-related nucleic acids.

9 Claims, 42 Drawing Sheets

OTHER PUBLICATIONS

Lubahn, D., et al., Science, 240:327 (1988).
Mullis, Cold Spring Harbor Symposia on Quantitative Biology, Cold Spring Harbor Laboratory (New York, USA) vol. LI (Published 1986) pp. 263–273.
Saiki, et al., Nature (London UK), 324:163–166 (1986).
Trapman, et al., Biochemical & Biophysical Research Communications, 153:241–248 (1988).
Chang, et al., BBRC, 155:971–977 (1988).
Chang, et al., Steroid/Thyroid . . . , Birkhauser Verlag, Basal, pp. 183–193 (1988).
Hazel, et al., Proc. Nat'l. Acad. Sci. (USA), 85:8444–8448 (1988).
Lubahn et al., Science 240:327–330 (1988).
Govindan et al., Progress in Cancer Res. & Therapy 35:49–54 (1988).
Trapman et al., Biochem. Biophy. Res. Commun. 153:241–248 (1988).
Ryseck et al., EMBO J, 8(11):3327–3335, 1989.
Lubhan et al., PNAS, 86:9534–9538, 1989.
Tilley et al., PNAS, 86:327–331, 1989.
Lubahn et al., Mol Endocrinol, 2(12):1276–1285, 1988.
Tan et al., Mol Endocrinol, 2(12):1276–1285, 1988.
International Search Report.
Walter et al., Proc. Natl. Acad. Sci. 82:7889–7893 (1985).

```
hAR    1:                                           GAATTCCGGCGGAGAGAGAACCCTCTGTTTTCCCCACTCTCTCTCCACCTCCTCCT
hAR   56: GCCTTCCCCACCCCGAGTGCGGAGCAGAGATCAAAAGGATGAAAAGGCAGTCAGTCTTCAGTAGCCAAAAAAC
hAR  129: AAAACAAACAAAACAAAAAGCCGAATTTGGAGGATTTGTTTTCTTTTAAGATAATAACTCAGTTCTTATTTGCACTACTTCA
hAR  202: GTGGACACTGAATTTGGAGGTGGAGGTGGAGGTGGAGGTGAGCCTAGCAGTGTGAGCCTAGCCTAGCAGGGCAGATCTGGGCATCTTTTGAATCTACCC
hAR  275: TTCAAGTATTAAGAGACAGACTGTGAGCCTAGCAGTGTGAGCCTAGCCTAGCAGGCAGATCTGTCCCACCGTGTCTTCTTTCTGCACGAG
hAR  348: ACTTTGAGGCTGTGTCAGAGGCGCTTTTGCGTGGTTGCTCCCGCAAGTTTCCTTCTCTTGGAGCTTCCCGCAGGTG
hAR  421: GGCAGCTAGCTGCAGCGACTACCGCATCATCACAGCCTGTTGAACTCTTCTTGAGCAAGAGAAGGGGAGGCGGG rAR    1:                GAATTCGGTGGAAGCTAGAGACAAGCTAAAGG
rAR    1:                GTAAGG---G-A------A-TC--C------C--
hAR  494:                                    Met Glu Val Gln Leu Gly Leu Gly
hAR    1:                                    ATG GAG GTG CAG TTA GGG CTG GGA
                                                       --A -- -- -- -- -- -- rAR    9: Arg Val Tyr Pro Arg Pro Pro Ser Lys Thr Tyr Arg Gly Ala Phe Gln Asn Leu
rAR   57: AGG GTC TAC CCA CGG CCC CCG TCC AAG ACC TAT CGA GGA GCG TTC CAG AAT CTG
hAR  556: --- --- --- --T --- --- --G --- --- --- --C --- --- --- --T --- --- ---
hAR    9:  -   -   -   -   -   -   -   -   -   -   -   -   -   -   -   -   -   - rAR   27: Phe Gln Ser Val Arg Glu Ala Ile Gln Asn Pro Gly Pro Arg His Pro Glu Ala
rAR  111: TTC CAG AGC GTG CGC GAA GCG ATC CAG AAC CCG GGC CCC AGG CAC CCT GAG GCC
hAR  610: --- --- --- --- --- --- --- --- --- --- --- --- --- --- --- --A --- ---
hAR  271:  -   -   -   -   -  Val  -   -   -   -   -   -   -   -   -   -   -   -
```

FIG. 3A

```
rAR  45: Ala Ser Ile Ala Pro Pro Gly Ala Cys Leu ... ... ... ... Gln Gln Arg Gln
rAR 165: GCT AGC ATA GCA CCT CCC GGT GCC TGT TTA ... ... ... ... CAG CAG CGG CAG
hAR 664: --G --- --- GC- --- --- --C --- A-- --G CTG CTG --- -A- --- --- CAG
hAR  45: --- --- --- Ala --- --- --- --- Ser --- Leu Leu Leu --- Gln --- --- Gln rAR  59: ... ... ... ... ... ... ... ... ... ... Glu Thr Ser Pro Arg  Arg
rAR 207: ... ... ... ... ... ... ... ... ... ... GAG ACT AGC CCC CGG  CGG
hAR 718: CAG CAG CAG CAG CAG CAG CAG CAG CAG CAA --- --- --- --- A--  -A-
hAR  63: Gln Gln Gln Gln Gln Gln Gln Gln Gln Gln --- --- --- --- ---  Gln rAR  65: Arg Arg Gln Gln His Pro Glu Asp Gly Ser Pro Gln Ala His Ile Arg Gly
rAR 225: CGG CGG CAG CAG CAC CCT GAG GAT GGC TCT CCT CAA GCC CAC ATC AGA GGC
hAR 772: -A- -A- --- --- --- --- --- GG- --- --- --- --C --- --- --T CGT ---
hAR  81: Gln Gln --- --- --- --- --- Gly --- --- --- --- --- --- --- Arg --- rAR  83: Thr Thr Gly Tyr Leu Ala Leu Glu Glu Gln Gln Gln Gln Pro Ser Gln Gln Gln Ser
rAR 279: ACC ACA GGC TAC CTG GCC CTG GAG GAG CAG CAG CAG CAG CCT TCA CAG CAG CAG TCA
hAR 823: C-- --- --- --- --- --- -T- --- --T --- --- --- --- --A --- --C --- --- --G
hAR  98: Pro --- --- --- --- --- Val --- Asp --- --- --- --- Pro --- --- --- --- --- rAR 101: Ala Ser Glu Gly His Pro Glu Ser Gly Cys Leu Pro Glu Pro Gly Ala Ala Thr
rAR 333: GCC TCC GAG GGC CAC CCT GAG AGC GGC TGC CTC CCG GAG CCT GGA GCT GCC ACG
hAR 877: --- CTG --- T-- --- --C --- -A- --T G-- -A- --- --- --- --- --C --- GT-
hAR 116: --- Leu --- Cys --- --- --- Arg --- Val --- --- --- --- --- --- --- Val
```

FIG. 3B

```
rAR 119:   Ala Pro Gly Lys Gly Leu Pro Gln Pro Ala Pro Pro Asp Gln Asp Asp
rAR 387:   GCT CCT GGC AAG GGG CTG CCG CAG CCA GCT CCT CCA GAT CAG GAT GAC
hAR 931:   --C G-C A-- --- --- --- --- --- --A --- --- -G- --C G-- --- ---
hAR 134:    -  Ala Ser  -   -   -   -  Leu  -   -   -  -G-  -  Glu  -   - rAR 137:   Ser Ala Ala Pro Ser Thr Leu Ser Leu Leu Gly Pro Thr Phe Pro Gly Leu Ser
rAR 441:   TCA GCT GCC CCA TCC ACG TTG TCC CTA CTG GGC CCC ACT TTC CCA GGC TTA AGC
hAR 985:   --- --- --- --- --- --- --- --- --- --G --- --- --- --- --C --- --- ---
hAR 152:    -   -   -   -   -   -   -   -   -   -   -   -   -   -   -   -   -   - rAR 155:   Ser Cys Ser Ala Asp Ile Lys Asp Ile Leu Ser Glu Ala Gly Thr Met Gln Leu
rAR 495:   AGC TGC TCC GCA GAC ATT AAA GAC ATC CTG AGC GAG GCC GGC ACC ATG CAA CTT
hAR1039:   --- --- --- --T --- --- C-- --- --- --- --- --- --- --- A-- --- --- --C
hAR 170:    -   -   -   -   -   -  Leu  -   -   -   -   -   -   -  Ser  -   -   - rAR 173:   Leu Gln Gln Gln Gln Gln Gln Gln Gln Gln Gln Gln Gln Gln Gln Gln Gln Gln
rAR 549:   CTT CAG CAG CAG CAA CAG CAA CAG CAG CAG CAG CAG CAG CAG CAG CAG CAG CAG
hAR1093:   --- --- --A --- --- --G --- --- --- ::: ::: ::: ::: ::: ::: ::: ::: :::
hAR 188:    -   -   -   -   -   -   -   -   -   .   .   .   .   .   .   .   .   .

rAR 191:   Gln Gln Gln Gln Glu Val Ile Ser Glu Gly Ser Ser Ser Val Arg Ala Arg
rAR 603:   CAG CAA CAG CAG GAG GTA ATA TCC GAA GGC AGC AGC AGC GTG AGA GCA AGG
hAR1111:   ::: ::: ::: ::: --A -C- G-- --- --- --- --- --- --- -G- --- --G ---
hAR 194:    .   .   .   .   -  Ala Val  -   -   -   -   -   -  Gly  -   -   -
```

FIG. 3C

```
rAR 209:  Glu Ala Thr Gly Ala Pro Ser Ser Ser Lys Asp Ser Tyr Leu Gly Gly Asn Ser
rAR 657:  GAG GCC ACT GGG GCT CCC TCT TCC TCC AAG GAT AGT TAC CTA GGG GGC AAT TCG
hAR1150:  --- --- T-G --- --- --- A-- --- --- --- --C --- --- T-- --- --- -C- ---
hAR 207:  --- --- Ser --- --- --- --- Thr --- --- Asn --- --- --- --- --- Thr --- rAR 227:  Thr Ile Ser Asp Ser Ala Lys Glu Leu Cys Lys Val Ala Val Ser Val Ser Met Gly
rAR 711:  ACC ATA TCT GAC AGT GCC AAG GAG TTG TGT AAA GCA GTG TCT GTG TCC ATG GGG
hAR1204:  --- --T --- --- -AC --- --- --- --- --- --G --- --- --- --G --- --- --C
hAR 225:  --- --- --- --- Asn --- --- --- --- --- --- --- --- --- --- --- --- --- rAR 245:  Leu Gly Val Glu Ala Leu Glu His Leu Ser Pro Gly Glu Gln Leu Arg Gly Asp
rAR 765:  TTG GGT GTG GAA GCA CTG GAA CAT CTG AGT CCA GGG GAG CAG CTT CGG GGC GAC
hAR1258:  C-G --- --- --- --- --G T-- --G --- --- --- --- --- --A --- --- --G --T
hAR 243:  --- --- --- --- --- --- --- --- --- --- --- --- --- --- --- --- --- --- rAR 263:  Cys Met Tyr Ala Ser Leu Leu Gly Gly Pro Pro Ala Val Arg Pro Thr Pro Cys
rAR 819:  TGC ATG TAC GCG TCG CTC CTG GGA GGT CCA CCC GCC GTG CGT CCC ACT CCT TGT
hAR1312:  --- --- --- --C C-A --T T-- --- -T- --- --- --- --T --- --- --- --- ---
hAR 261:  --- --- --- --- Pro --- Val --- --- --- --- --- --- --- --- --- --- --- rAR 281:  Ala Pro Leu Ala Glu Cys Lys Gly Leu Ser Leu Asp Glu Gly Pro Gly Lys Gly
rAR 873:  GCG CCT CTG GCC GAA TGC AAA GGT CTT TCC CTG GAC GAA GGC CCG GGC AAA GGC
hAR1366:  --C --- --A T-- --- --- --- --- TC- CTG --A --- --C A-- G-A --- --G A--
hAR 279:  --- --- --- --- --- --- --- --- Ser Leu --- --- Asp Ser Ala --- --- Ser
```

FIG. 3D

| | | | | | | | | | | | | | | | | | | |
|---|---|---|---|---|---|---|---|---|---|---|---|---|---|---|---|---|---|---|
| rAR 299: | Thr | Glu | Glu | Thr | Ala | Glu | Tyr | Ser | Ser | Phe | Lys | Gly | Gly | Tyr | Ala | Lys | Gly | Leu |
| rAR 927: | ACT | GAA | GAG | ACT | GCT | GAG | TAT | TCC | TCT | TTC | AAG | GGA | GGT | TAC | GCC | AAA | GGG | TTG |
| hAR1420: | --- | --- | --- | --T | --- | --- | --- | --- | C-- | --- | --- | --- | --- | --- | A-- | --- | --- | C-A |
| hAR 297: | --- | --- | --- | Asp | --- | --- | --- | --- | Pro | --- | --- | --- | --- | --- | Thr | --- | --- | --- |

| | | | | | | | | | | | | | | | | | | |
|---|---|---|---|---|---|---|---|---|---|---|---|---|---|---|---|---|---|---|
| rAR 317: | Glu | Gly | Glu | Ser | Leu | Gly | Cys | Ser | Ser | Gly | Ser | Ser | Glu | Ala | Gly | Ser | Ser | Gly | Thr |
| rAR 981: | GAA | GGT | GAG | AGT | CTG | GGC | TGC | TCT | TCT | GGC | AGC | AGT | GAA | GCA | GGT | AGC | TCT | GGG | ACA |
| hAR1474: | --- | --- | --- | --C | --- | --- | --A | --- | --- | --- | --- | --- | GC- | -C- | --G | --- | --C | --- | --- |
| hAR 315: | --- | --- | --- | --- | --- | --- | --- | --- | --- | --- | --- | --- | Ala | Ala | --- | --- | --- | --- | --- |

| | | | | | | | | | | | | | | | | | | |
|---|---|---|---|---|---|---|---|---|---|---|---|---|---|---|---|---|---|---|
| rAR 335: | Leu | Glu | Ile | Pro | Ser | Ser | Leu | Tyr | Lys | Ser | Gly | Ala | Val | Asp | Glu | Ala |
| rAR1035: | CTT | GAG | ATC | CCG | TCC | TCA | CTG | TAT | AAG | TCT | GGA | GCA | GTA | GAC | GAG | GCA |
| hAR1528: | --- | --A | C-G | --- | --- | --T | A-C | --C | --- | --C | --- | --- | C-G | --- | --- | --- |
| hAR 333: | --- | --- | Leu | --- | --- | Thr | --- | --- | --- | --- | --- | --- | Leu | --- | --- | --- |

| | | | | | | | | | | | | | | | | | | |
|---|---|---|---|---|---|---|---|---|---|---|---|---|---|---|---|---|---|---|
| rAR 353: | Ala | Ala | Tyr | Gln | Asn | Arg | Asp | Tyr | Tyr | Asn | Phe | Pro | Leu | Ala | Leu | Ser | Gly | Pro |
| rAR1089: | GCA | GCA | TAC | CAG | AAT | CGC | GAC | TAC | TAC | AAC | TTT | CCG | CTC | GCT | CTG | TCC | GGG | CCG |
| hAR1582: | --T | --- | --G | --- | --- | -G- | --- | --- | --- | --- | --- | --- | --A | --G | --- | G-- | --A | --- |
| hAR 351: | --- | --- | --- | --- | --- | Ser | --- | --- | --- | --- | --- | --- | --- | Ala | --- | --- | --- | --- |

| | | | | | | | | | | | | | | | | | | |
|---|---|---|---|---|---|---|---|---|---|---|---|---|---|---|---|---|---|---|
| rAR 371: | Pro | His | Pro | Pro | Pro | Pro | Thr | His | Pro | His | Ala | Arg | Ile | Lys | Leu | Glu | Asn | Pro |
| rAR1143: | CCG | CAC | CCC | CCG | CCC | CCT | ACC | CAT | CCA | CAC | GCC | CGC | ATC | AAG | CTG | GAG | AAC | CCG |
| hAR1636: | --- | --C | --C | --T | --- | --G | --- | C-- | --- | --- | --- | --- | --- | --- | --T | --- | --- | --- |
| hAR 369: | --- | Pro | --- | --- | --- | --- | --- | Pro | --- | --- | --- | --- | --- | --- | --- | --- | --- | --- |

FIG. 3E

|  | | | | | | | | | | | | | | | | | | |
|---|---|---|---|---|---|---|---|---|---|---|---|---|---|---|---|---|---|---|
| rAR 389: | Leu | Asp | Tyr | Gly | Ser | Ala | Trp | Ala | Ala | Ala | Ala | Gln | Cys | Arg | Tyr | Gly | Asp |
| rAR1197: | TTG | GAC | TAC | GGC | AGC | GCC | TGG | GCT | GCG | GCA | GCG | CAA | TGC | CGC | TAT | GGG | GAC |
| hAR1690: | C-- | --- | --- | --- | --- | --- | --- | --- | -G- | --- | --T | --G | --- | --- | --- | --- | --- |
| hAR 387: | --- | --- | --- | --- | --- | --- | --- | --- | --- | --- | --- | --- | --- | --- | --- | --- | --- |

|  | | | | | | | | | | | | | | | | | |
|---|---|---|---|---|---|---|---|---|---|---|---|---|---|---|---|---|---|
| rAR 407: | Leu | Ala | Ser | Leu | His | Gly | Gly | Ser | Val | Ala | Gly | Pro | Ser | Thr | Gly | Ser | Pro | Pro |
| rAR1251: | TTG | GCT | AGC | CTA | CAT | GGA | GGG | AGT | GTA | GCC | GGA | CCC | AGC | ACT | GGA | TCG | CCC | CCA |
| hAR1744: | C-- | --G | --- | --G | --- | --C | G-- | --C | G-- | --- | --- | --- | G-T | T-- | --G | --A | --- | T-- |
| hAR 405: | Leu | --- | --- | --- | --- | --- | --- | --- | Ala | Gly | Ala | --- | Gly | Ser | --- | --- | --- | Ser |

|  | | | | | | | | | | | | | | | | | |
|---|---|---|---|---|---|---|---|---|---|---|---|---|---|---|---|---|---|
| rAR 425: | Ala | Thr | Ala | Ser | Ser | Ser | Trp | His | Thr | Leu | Phe | Thr | Ala | Glu | Glu | Gly | Gln | Leu |
| rAR1305: | GCC | ACC | GCC | TCT | TCT | TCC | TGG | CAT | ACT | CTC | TTC | ACA | GCT | GAA | GAA | GGC | CAA | TTA |
| hAR1798: | --- | --- | G-- | --T | --C | --A | --- | --- | --- | --- | --- | --C | --- | --- | --- | --- | --G | --G |
| hAR 423: | --- | --- | Ala | --- | --- | --- | --- | --- | --- | --- | --- | --- | --- | --- | --- | --- | --- | --- |

|  | | | | | | | | | | | | | | | | | |
|---|---|---|---|---|---|---|---|---|---|---|---|---|---|---|---|---|---|
| rAR 443: | Tyr | Gly | Pro | Gly | Gly | Gly | Gly | Gly | ... | ... | ... | Ser | Ser | Ser | Pro | Asp | Ala | Gly | Pro | Val |
| rAR1359: | TAT | GGG | CCA | GGA | GGC | GGG | GGC | GGC | ... | ... | ... | AGC | AGT | AGC | CCA | GAT | GCT | GGG | CCT | GTA |
| hAR1852: | --- | --A | T-T | --T | --T | --- | --- | --G | ... | ... | ... | G-- | G-C | G-- | --- | G-C | G-- | --G | -AA | G-- |
| hAR 441: | --- | --- | Cys | --- | --- | --- | --- | --- | ... | ... | ... | --- | --- | --- | --- | --- | --- | --- | Glu | Ala |

|  | | | | | | | | | | | | | | | | |
|---|---|---|---|---|---|---|---|---|---|---|---|---|---|---|---|---|---|
| rAR 451: | ... | ... | ... | ... | ... | ... | ... | ... | ... | ... | ... | ... | ... | ... | ... | ... | ... |
| rAR1383: | ... | ... | ... | ... | ... | ... | ... | ... | ... | ... | ... | ... | ... | ... | ... | ... | ... |
| hAR1906: | GGC | GGG | GGC | GGC | GGC | GGC | GGC | GGC | GGC | G-- | G-C | G-- | GGC | G-- | GGC | GGC | GGC |
| hAR 459: | Gly | Gly | Gly | Gly | Gly | Gly | Gly | Gly | Gly | Gly | Gly | Gly | Gly | Gly | Gly | Gly | Gly |

FIG. 3F

| | | | | | | | | | | | | | | | | | | | |
|---|---|---|---|---|---|---|---|---|---|---|---|---|---|---|---|---|---|---|---|
| rAR 461: | Ala | Pro | Tyr | Gly | Tyr | Thr | Arg | Pro | Pro | Gln | Gly | Leu | Ala | Ser | Gln | Glu | Gly | Asp |
| rAR1413: | GCC | CCC | TAT | GGC | TAC | ACT | CGG | CCC | CCT | CAG | GGG | CTG | GCA | AGC | CAG | GAG | GGT | GAC |
| hAR1960: | --- | --- | --- | --C | --- | --- | --- | --- | --- | --- | --- | --- | --G | G-- | --- | --A | A-C |
| hAR 477: | | | | | | | | | | | | | | Gly | | | Ser |

| | | | | | | | | | | | | | | | | | | | |
|---|---|---|---|---|---|---|---|---|---|---|---|---|---|---|---|---|---|---|---|
| rAR 479: | Phe | Ser | Ala | Ser | Glu | Val | Trp | Tyr | Pro | Gly | Val | Val | Asn | Arg | Val | Pro | Tyr |
| rAR1467: | TTC | TCT | GCC | TCT | GAA | GTG | TGG | TAT | CCT | GGT | GGA | GTT | GTG | AAC | AGA | GTC | CCC | TAT |
| hAR2014: | --- | A-C | --A | C-- | --T | --- | --- | --- | --C | --- | --- | A-G | --- | --- | -G- | --- | --G | --- |
| hAR 495: | | Thr | | Pro | Asp | | | | | | | Met | | | Ser |

| | | | | | | | | | | | | | | | | | | | |
|---|---|---|---|---|---|---|---|---|---|---|---|---|---|---|---|---|---|---|---|
| rAR 497: | Pro | Ser | Pro | Ser | Cys | Val | Lys | Ser | Glu | Met | Gly | Pro | Trp | Met | Glu | Asn | Tyr | Ser |
| rAR1521: | CCC | AGT | CCC | AGT | TGT | GTT | AAA | AGT | GAA | ATG | GGA | CCT | TGG | ATG | GAG | AAC | TAC | TCC |
| hAR2068: | --- | --- | --- | -C- | --- | --C | --- | --- | --C | --- | --- | --C | --- | --- | --T | -G- | --- | --- |
| hAR 513: | | Thr | | | | | | | | | | | | | Asp | Ser |

| | | | | | | | | | | | | | | | | | | | |
|---|---|---|---|---|---|---|---|---|---|---|---|---|---|---|---|---|---|---|---|
| rAR 515: | Gly | Pro | Tyr | Gly | Asp | Met | Arg | Leu | Asp | Ser | Thr | Arg | Asp | His | Val | Leu | Pro | Ile |
| rAR1575: | GGA | CCT | TAT | GGG | GAC | ATG | CGT | TTG | GAC | AGT | ACC | AGG | GAC | CAC | GTT | TTA | CCC | ATC |
| hAR2122: | --- | --- | --C | --- | --- | --- | --- | --- | --G | -C- | G-- | --- | --- | --- | --- | --T | --G | --T |
| hAR 531: | | | | | | | | | | Glu | Thr | Ala |

| | | | | | | | | | | | | | | | | | | | |
|---|---|---|---|---|---|---|---|---|---|---|---|---|---|---|---|---|---|---|---|
| rAR 533: | Asp | Tyr | Tyr | Phe | Pro | Pro | Gln | Lys | Thr | Cys | Leu | Ile | Cys | Gly | Asp | Glu | Ala | Ser |
| rAR1629: | GAC | TAT | TAC | TTC | CCA | CCC | CAG | AAG | ACC | TGC | CTG | ATC | TGT | GGA | GAT | GAA | GCT | TCT |
| hAR2176: | --- | --- | --- | --T | --- | --- | --- | --- | --- | --- | --- | --- | --- | --- | --- | --- | --- | --- |
| hAR 549: | | | | | | | | | | | | | | | | | | |

| | | | | | | | | | | | | |
|---|---|---|---|---|---|---|---|---|---|---|---|---|
| rAR 641: | Lys | Met | Thr | Val | Ser | His | Ile | Glu | Gly | Tyr | Glu | Cys | Gln | Pro | Ile | Phe | Leu | Asn |
| rAR1953: | AAG | ATG | ACT | GTA | TCA | CAC | ATT | GAA | GGC | TAT | GAA | TGT | CAA | CCT | ATC | TTT | CTT | AAT |
| hAR2500: | --- | --- | --A | --G | --- | --- | --- | --- | --- | --- | --- | --- | --G | --C | --- | --- | --G | --- |
| hAR 657: | | | Leu | | | | | | | | | | | | | | | |

| rAR 659: | Val | Leu | Glu | Ala | Ile | Glu | Pro | Gly | Val | Val | Cys | Ala | Gly | His | Asp | Asn | Asn | Gln |
|---|---|---|---|---|---|---|---|---|---|---|---|---|---|---|---|---|---|---|
| rAR2007: | GTC | CTG | GAA | GCC | ATT | GAG | CCA | GGA | GTG | GTG | TGT | GCC | GGA | CAT | GAC | AAC | AAC | CAG |
| hAR2554: | --- | --- | --- | --- | --- | --- | --- | --- | --T | --A | --- | --- | --- | --T | --- | --- | --- | --- |
| hAR 675: | | | | | | | | | | | | | | | | | | |

| rAR 677: | Pro | Asp | Ser | Phe | Ala | Ala | Leu | Leu | Ser | Ser | Leu | Asn | Glu | Leu | Gly | Glu | Arg | Gln |
|---|---|---|---|---|---|---|---|---|---|---|---|---|---|---|---|---|---|---|
| rAR2061: | CCT | GAT | TCC | TTT | GCT | GCC | TTG | TTA | TCT | AGT | CTC | AAC | GAG | CTT | GGC | GAG | AGA | CAG |
| hAR2608: | --C | --- | --- | --- | --A | --- | --- | --- | C-C | --- | --- | --T | --- | --- | --A | --- | --- | --- |
| hAR 693: | | | | | | | | | | | | | | | | | | |

| rAR 695: | Leu | Val | His | Val | Val | Lys | Trp | Ala | Lys | Ala | Leu | Pro | Gly | Phe | Arg | Asn | Leu | His |
|---|---|---|---|---|---|---|---|---|---|---|---|---|---|---|---|---|---|---|
| rAR2115: | CTT | GTA | CAT | GTG | GTC | AAG | TGG | GCC | AAG | GCC | TTG | CCT | GGC | TTC | CGC | AAC | TTG | CAT |
| hAR2662: | --- | --- | --C | --- | --- | --- | --- | --- | --- | --- | --- | --- | --- | --- | --- | --- | --A | --C |
| hAR 711: | | | | | | | | | | | | | | | | | | |

| rAR 713: | Val | Asp | Asp | Gln | Met | Ala | Val | Ile | Gln | Tyr | Ser | Trp | Met | Gly | Leu | Met | Val | Phe |
|---|---|---|---|---|---|---|---|---|---|---|---|---|---|---|---|---|---|---|
| rAR2169: | GTG | GAT | GAC | CAG | ATG | GCA | GTC | ATT | CAG | TAT | TCC | TGG | ATG | GGA | CTG | ATG | GTA | TTT |
| hAR2716: | --- | --- | --C | --- | --- | --T | --- | --- | --- | --C | --- | --- | --- | --G | --C | --- | --A | --G |
| hAR 729: | | | | | | | | | | | | | | | | | | |

| | | | | | | | | | | | | |
|---|---|---|---|---|---|---|---|---|---|---|---|---|
| rAR 731: | Ala | Met | Gly | Trp | Arg | Ser | Phe | Thr | Asn | Val | Asn | Ser | Arg | Met | Leu | Tyr | Phe | Ala |
| rAR2223: | GCC | ATG | GGT | TGG | CGG | TCC | TTC | ACT | AAT | GTC | AAC | TCT | AGG | ATG | CTC | TAC | TTT | GCA |
| hAR2770: | --- | --- | --C | --- | --A | --- | --- | --C | --- | --- | --- | --C | --- | --- | --- | --C | --- | --C |
| hAR 747: | | | | | | | | | | | | | | | | | | |

| | | | | | | | | | | | | |
|---|---|---|---|---|---|---|---|---|---|---|---|---|
| rAR 749: | Pro | Asp | Leu | Val | Phe | Asn | Glu | Tyr | Arg | Met | His | Lys | Ser | Arg | Met | Tyr | Ser | Gln |
| rAR2277: | CCT | GAC | CTG | GTT | TTC | AAT | GAG | TAT | CGC | ATG | CAC | AAG | TCT | CGA | ATG | TAC | AGC | CAG |
| hAR2824: | --T | --- | --- | --- | --- | --- | --- | --- | --- | --- | --- | --- | --- | --G | --- | --- | --- | --- |
| hAR 765: | | | | | | | | | | | | | | | | | | |

| | | | | | | | | | | | | |
|---|---|---|---|---|---|---|---|---|---|---|---|---|
| rAR 767: | Cys | Val | Arg | Met | Arg | His | Leu | Ser | Gln | Glu | Phe | Gly | Trp | Leu | Gln | Ile | Thr | Pro |
| rAR2331: | TGC | GTG | AGG | ATG | AGG | CAC | CTT | TCT | CAA | GAG | TTT | GGA | TGG | CTC | CAG | ATA | ACC | CCC |
| hAR2878: | --T | --- | --C | --- | C-A | --- | --- | --- | --- | --- | --- | --- | --- | --- | --A | --C | --- | --- |
| hAR 783: | | | | | | | | | | | | | | | | | | |

| | | | | | | | | | | | | |
|---|---|---|---|---|---|---|---|---|---|---|---|---|
| rAR 785: | Gln | Glu | Phe | Leu | Cys | Met | Lys | Ala | Leu | Leu | Leu | Phe | Ser | Ile | Ile | Pro | Val | Asp |
| rAR2385: | CAG | GAA | TTC | CTG | TGC | ATG | AAA | GCA | CTG | CTA | CTC | TTC | AGC | ATT | ATT | CCA | GTG | GAT |
| hAR2932: | | | | | | | | | | | | | | | | | | |
| hAR 801: | | | | | | | | | | | | | | | | | | |

| | | | | | | | | | | | | |
|---|---|---|---|---|---|---|---|---|---|---|---|---|
| rAR 803: | Gly | Leu | Lys | Asn | Gln | Lys | Phe | Asp | Glu | Leu | Arg | Met | Asn | Tyr | Ile | Lys | Glu |
| rAR2439: | GGG | CTG | AAA | AAT | CAA | AAA | TTC | GAT | GAA | CTT | CGA | ATG | AAC | TAC | ATC | AAG | GAA |
| hAR2986: | | | | | | | | | | | | | | | | | | |
| hAR 819: | | | | | | | | | | | | | | | | | | |

FIG. 3J

```
rAR  821:  Leu Asp Arg Ile Ile Ala Cys Lys Arg Lys Asn Pro Thr Ser Cys Ser Arg Arg
rAR2493:   CTT GAT CGC ATC ATT GCA TGC AAA AGA AAA AAT CCC ACA TCC TGC TCA AGG CGC
rAR3040:   --C --- --- --- --T --- --- --- --- --- --- --- --- --- --- --- --- --A
hAR  837:  --- --- --- --- --- --- --- --- --- --- --- --- --- --- --- --- --- --- rAR  839:  Phe Tyr Gln Leu Thr Lys Leu Leu Asp Ser Val Gln Pro Ile Ala Arg Glu Leu
rAR2547:   TTC TAC CAG CTC ACC AAG CTC CTG GAT TCT GTG CAG CCT ATT GCA AGA GAG CTG
hAR3094:   --- --- --- --- --- --- --- --- --- --C --- --- --- --- --G --- --- ---
hAR  855:  --- --- --- --- --- --- --- --- --- --- --- --- --- --- --- --- --- --- rAR  857:  His Gln Phe Thr Phe Asp Leu Leu Ile Lys Ser His Met Val Ser Val Asp Phe
rAR2601:   CAT CAA TTC ACT TTT GAC CTG CTA ATC AAG TCC CAT ATG GTG AGC GTG GAC TTT
hAR3148:   --- --G --- --- --- --- --- --- --- --- --A --- --C --- --- --- --- ---
hAR  873:  --- --- --- --- --- --- --- --- --- --- --- --- --- --- --- --- --- --- rAR  875:  Pro Glu Met Met Ala Glu Ile Ile Ser Val Gln Val Pro Lys Ile Leu Ser Gly
rAR2655:   CCT GAA ATG ATG GCA GAG ATC ATC TCT GTG CAA GTG CCC AAG ATC CTT TCT GGG
hAR3202:   --G --- --- --- --- --- --- --- --- --- --- --- --- --- --- --- --- ---
hAR  891:  --- --- --- --- --- --- --- --- --- --- --- --- --- --- --- --- --- --- rAR  893:  Lys Val Lys Pro Ile Tyr Phe His Thr Gln
rAR2709:   AAA GTC AAG CCC ATC TAT TTC CAC ACA CAG TGA AGATTTGGAAACCCTAATACCCAAACC
hAR3256:   --- --- --- --- --- --- --- --- --C --- --- ---------CA----------T-T--C-C--
hAR  909:  --- --- --- --- --- --- --- --- --- --- --- ---
```

FIG. 3K

```
rAR2769:  CACCTTGTTCCCTTTTCAGATGTCTTCTGCCTGTTATATAACTGCACTACTTCTCTGCAGTGCCTTGGG
hAR3316:  --G--CA-G---CC--TCAGATGTC-TCTG-CTG-TATA-CTCTGCACTACTCCTCTGCAGTGC-T-G--- rAR2840:  GGAAATTCCTCTACTGATGTACAGTCTGTCATGAACATGTTCCCCAGTTCTATTTCCTGGCTTTTCCTTC
hAR3387:  AATTTCCT--A-TGATG-AC-GTC-G-CATGGA-TTC-A--TG-TG-GCT-T---TT-CTCT--C--TCCT rAR2911:  TTTCTTTTTCTTCTCTGCCTCTTTTACCCTCCCATGGCACATTTTGAATCCGCTGCGTGTGTGCTCC
hAR3458:  --CT----CT-CT-C-CTCC-TATC-AAC--TC--ATG-CAC-T--CAGACT-TGCT-C-CAT-GTG----- rAR2982:  TGCCTGTGTGTTTGAGTTTTGTTGTATTTCTTCAAGTCTGTGATGATCTTCTTGTGGCCAGTGTCAACTGT
hAR3529:  -AT---------A-GG--------GC---T--A---------C--A-A---------G-TG rAR3053:  GCTTGTTTATAGCACTGTGCTGTGTGCCAACCAAGCAAATGTTTACTCACCTTATGCCATGGCAAGTTTAG
hAR3600:  TGC-TG--TACAGCACTACTCTGTGC-AGC-AC-CA--CGT--ACT-AT-T-ATGC-ACG--A-GT--AGA rAR3124:  AGAGCTATAAGTATCTTGGGAAGAAACAAACAGAGAGAGTAAAAAAACCAAAAAACAAAAAACAAAAAACCA
hAR3671:  GAGCTA-G-TTATCTGG--A--TC--A-C-A-A-C-CCCG--TTC rAR3195:  AAAAGCAAAAAAAAAAGGAATTC
```

FIG. 3L

```
     GAATTCGGGCCCGTGGGCTTTCTTCAACCCTCTCTTCCCGGAGCGCCCCAATCC                              55
     ACGAGTGGCAGCCGCGGGACTGTCGCGTCGGCCCGACGCGGGAGTCAGCAGGGGCGAAAAGCGGTAGATC             126

ATG GCA ACC ATA GAA GAA ATT GCA CAT CAA ATT ATT GAA CAA CAG ATG GGA GAG            180
  1: Met Ala Thr Ile Glu Glu Ile Ala His Gln Ile Ile Glu Gln Gln Met Gly Glu

ATT GTT ACA GAG CAG CAA ACT GGG CAG AAA ATC CAG ATT GTG ACA GCA CTT GAT            234
 19: Ile Val Thr Glu Gln Gln Thr Gly Gln Lys Ile Gln Ile Val Thr Ala Leu Asp

CAT AAT ACC CAA GGC AAG CAG TTC ATT CTG ACA AAT CAC GAC GGC TCT ACT CCA            288
 37: His Asn Thr Gln Gly Lys Gln Phe Ile Leu Thr Asn His Asp Gly Ser Thr Pro

AGC AAA GTC ATT CTG GCC AGG CAA GAT TCC ACT CCG GGA AAA GTT TTC CTT ACA            342
 55: Ser Lys Val Ile Leu Ala Arg Gln Asp Ser Thr Pro Gly Lys Val Phe Leu Thr

ACT CCA GAT GCA GCA GGT GTC AAC CAG TTA TTT TTT ACC ACT CCT GAT CTG TCT            396
 73: Thr Pro Asp Ala Ala Gly Val Asn Gln Leu Phe Phe Thr Thr Pro Asp Leu Ser

GCA CAA CAC CTG CAG CTC CTA ACA GAT AAT TCT CCA GAC CAA GGA CCA AAT AAG            450
 91: Ala Gln His Leu Gln Leu Leu Thr Asp Asn Ser Pro Asp Gln Gly Pro Asn Lys

GTT TTT GAT CTT TGC GTA GTA TGT GGA GAC AAA GCA TCA GGA CGT CAT TAT GGA            504
109: Val Phe Asp Leu Cys Val Val Cys Gly Asp Lys Ala Ser Gly Arg His Tyr Gly

GCA GTA ACT TGT GAA GGC TGC AAA GGA TTT TTT AAA AGA AGC ATC CGA AAA AAT            558
127: Ala Val Thr Cys Glu Gly Cys Lys Gly Phe Phe Lys Arg Ser Ile Arg Lys Asn
```

FIG. 4A

```
145: TTA GTA TAT TCA TGT CGA GGA TCA AAG GAT TGT ATT ATT AAT AAG CAC CAC CGA  612
     Leu Val Tyr Ser Cys Arg Gly Ser Lys Asp Cys Ile Ile Asn Lys His His Arg

163: AAC CGC TGT CAA TAC TGC AGG TTA CAG AGA TGT ATT GCG TTT GGA ATG AAG CAA  666
     Asn Arg Cys Gln Tyr Cys Arg Leu Gln Arg Cys Ile Ala Phe Gly Met Lys Gln

181: GAC TCT GTC CAA TGT GAA AGA AAA CCC ATT GAA GTA TCA CGA GAA AAA TCT TCC  720
     Asp Ser Val Gln Cys Glu Arg Lys Pro Ile Glu Val Ser Arg Glu Lys Ser Ser

199: AAC TGT GCC GCT TCA ACA GAA AAA ATC TAT ATC CGA AAG GAC CTT CGT AGC CCA  774
     Asn Cys Ala Ala Ser Thr Glu Lys Ile Tyr Ile Arg Lys Asp Leu Arg Ser Pro

217: TTA ACT GCA ACT CCA ACT TTT GTA GAT ACA AGT GAA AGT ACA AGG TCA ACA GGA  828
     Leu Thr Ala Thr Pro Thr Phe Val Asp Thr Ser Glu Ser Thr Arg Ser Thr Gly

235: CTG TTA GAT TCA GGA ATG TTC ATG AAT ATT CAT CCA TCT GGA GTA AAA ACT GAG  882
     Leu Leu Asp Ser Gly Met Phe Met Asn Ile His Pro Ser Gly Val Lys Thr Glu

253: TCA GCT GTG CTG ATG ACA TCA GAT AAG GCT GAA TCA TGT CAG GGA GAT TTA AGT  936
     Ser Ala Val Leu Met Thr Ser Asp Lys Ala Glu Ser Cys Gln Gly Asp Leu Ser

271: ACA TTG GCC AAT GTG GTT ACA TCA TTA GCG AAT CTT GGA AAA ACT AAA GAT CTT  990
     Thr Leu Ala Asn Val Val Thr Ser Leu Ala Asn Leu Gly Lys Thr Lys Asp Leu

289: TCT CAA AAT AGT AAT GAA ATG ATT TCT ATG AGC TTA AGC AAT GAT GAT ACC     1044
     Ser Gln Asn Ser Asn Glu Met Ile Ser Met Ser Leu Ser Asn Asp Asp Thr
```

FIG. 4B

```
307: TCT TTG TGT GAA TTT CAA GAA ATG CAG ACC AAC GGT GAT GTT TCA AGG GCA TTT 1098
     Ser Leu Cys Glu Phe Gln Glu Met Gln Thr Asn Gly Asp Val Ser Arg Ala Phe

325: GAC ACT CTT GCA AAA GCA TTG AAT CCT GGA GAG AGC ACA GCC TGC CAG AGC TCA 1152
     Asp Thr Leu Ala Lys Ala Leu Asn Pro Gly Glu Ser Thr Ala Cys Gln Ser Ser

343: GTA GCG GGC ATG GAA GGA AGT GTA CAC CTA ATC ACT GGA GAT TCA AGC ATA AAT 1206
     Val Ala Gly Met Glu Gly Ser Val His Leu Ile Thr Gly Asp Ser Ser Ile Asn

361: TAC ACC GAA AAA GAG GGG CCA CTT CTC AGC GAT TCA CAT GTA GCT TTC AGG CTC 1260
     Tyr Thr Glu Lys Glu Gly Pro Leu Leu Ser Asp Ser His Val Ala Phe Arg Leu

379: ACC ATG CCT TCT CCT ATG CCT GAG TAC CTG AAT GTG CAC TAC ATT GGG GAG TCT 1314
     Thr Met Pro Ser Pro Met Pro Glu Tyr Leu Asn Val His Tyr Ile Gly Glu Ser

397: GCC TCC AGA CTG CTG TTC TTA TCA ATG CAC TGG GCA CTT TCG ATT CCT TCT TTC 1368
     Ala Ser Arg Leu Leu Phe Leu Ser Met His Trp Ala Leu Ser Ile Pro Ser Phe

415: CAG GCT CTA GGG CAA GAA AAC AGC ATA TCA CTG GTG AAA GCT TAC TGG AAT GAA 1422
     Gln Ala Leu Gly Gln Glu Asn Ser Ile Ser Leu Val Lys Ala Tyr Trp Asn Glu

433: CTT TTT ACT CTT GGT CTT GCC CAG TGC TGG CAA GTG ATG AAT GTA GCA ACT ATA 1476
     Leu Phe Thr Leu Gly Leu Ala Gln Cys Trp Gln Val Met Asn Val Ala Thr Ile

451: TTA GCA ACA TTT GTC AAT TGT CTT CAC AAT AGT CTT CAA CAA GAT GCC AAG GTA 1530
     Leu Ala Thr Phe Val Asn Cys Leu His Asn Ser Leu Gln Gln Asp Ala Lys Val
```

FIG. 4C

```
     ATT GCA GCC CTC ATT CAT TTC ACA AGA CGA GCA ATC ACT GAT TTA TAA ATGCTTA  1585
469: Ile Ala Ala Leu Ile His Phe Thr Arg Arg Ala Ile Thr Asp Leu ***

ACTATAGAATGGCTTATGACTACCCAAAACAGTGCCCCATCAACAAATGGGGAAAATTGCCTTTTGAGCTC  1656
AGGAATAAATTTATAAATTGGGGACTACCTTTTAGTTCTTTAGCATATTCTATTTCTTATTGTTTTATATAA  1727
TTTTTAAATCATTTGCTTCCTCCTTATGTTTAACAGCAGAGGGTAATCACCTTAAAATGTCATCAAAAAT  1798
AGATCTACTAGAAGGCAGCATCACATTCCCATCTTACTTATGGACTCCTACCCTGGTCATGTCTTATAT  1869
GCCTGTAATGGTTATAAAGCCTACCTTCAGGAAAGCTATGGTTGACTAATTACTAATGGATGGGTTTTAAA  1940
CATGTCCCTCTAC AATAAA TTAAAATCTTTCAATGTTTGAATATAATGTGGAGGTGTTTACCTGAGGGCCT  2011
CTCTATCTCCCCGAATTC                                                       2029

*: 11 of 30 TR2 clones have extra 429 bp insert here which create a termiantion codon
TAG.
GTATGTATTAGCTTTTAAGGGAGAAAATACTTTTTAAAGATTCCAGCAAACTACAAGAGTATTGAAATTAACAAATATGTCAAAT
ATGTATACTTTTTAGTTTACAGTTTTCCAACTAAAATATAAGAATACAGACCTACGTATGTACTTTTTATTTATTCAACTAATA
TTTATTGAATACCTGTGTAAAAAGCACGTATTTGTAGTTTGTGTTTGGCAAAAGAATGAGAGATGCAAATTGGTTGTTTTACT
AATCTAAAGCAACTTTGTTGAACTTGCACATAATTTCTAAAGATTGATGGTTATCTTTGGAGTTTAGTATGGTAGCCATGTCTCC
TATTAGCAGCATTAAGCTTACCTACAGCTTACATTTCTAATTGTCTGTAATCCTATATTGTGATATAATAGTTTAACACATTTTT
GTAG
```

FIG. 4D

1: GAATTCG

8: GCCCCGTCCGCTTTCTCTTCCCCGAGCCGAACCCCCAATCCACGAGTGCACCCCCGAGACTGTGTCCGGTCCCCCCACCCGAGTCCACCACCCGAAACCGGTAGATC

127: ATG GCA ACC ATA GAA GAA ATT GCA CAT CAA ATT ATT GAA CAA CAG ATG GGA GAG ATT GTT ACA GAG CAG CAA ACT GGG CAG AAA ATC CAG
  1: met ala thr ile glu glu ile ala his gln ile ile glu gln gln met gly glu ile val thr glu gln gln thr gly gln lys ile gln 217: ATT GTG ACA GCA CTT GAT CAT AAT ACC CAA GCC AAG CAG TTC ATT CTG ACA AAT CAC GAC GCC TCT ACT CCA AGC AAA GTC ATT CTG GCC
 31: ile val thr ala leu asp his asn thr gln ala lys gln phe ile leu thr asn his asp ala ser thr pro ser lys val ile leu ala 307: AGG CAA GAT TCC ACT CCG GGA AAA GTT TTC CTT ACA ACT CCA GAT GCA GCA GGT GTC AAC CAG TTA TTT TTT ACC ACT CCT GAT CTG TCT
 61: arg gln asp ser thr pro gly lys val phe leu thr thr pro asp ala ala gly val asn gln leu phe phe thr thr pro asp leu ser

FIG. 5A

397: GCA CAA CAC CTG CAG CTC CTA ACA GAT AAT TCT CCA GAC CAA GGA CCA AAT AAG GTT TTT GAT CTT TGC GTA GTA TGT GGA GAC AAA GCA
91: ala gln his leu gln leu thr asp asn ser pro asp gln gly pro asn lys val phe asp leu cys val val cys gly asp lys ala 487: TCA GGA CGT CAT TAT GGA GCA GTA ACT TGT GAA GGC TGC AAA GGA TTT TTT AAA AGA AGC ATC CGA AAA AAT TTA GTA TAT TCA TGT CGA
121: ser gly arg his tyr gly ala val thr cys glu gly cys lys gly phe phe lys arg ser ile arg lys asn leu val tyr ser cys arg 577: GGA TCA AAG GAT TGT ATT ATT AAT AAG CAC CAC CGA AAC CGC TGT CAA TAC TGC AGG TTA CAG AGA TGT TTT GGA ATG AAG CAA
141: gly ser lys asp cys ile ile asn lys his his arg asn arg cys gln tyr cys arg leu gln arg cys phe gly met lys gln 667: GAC TCT GTC CAA TGT GAA AGA AAA CCC ATT GAA GTA CGA TCA CGA GAA AAA TCT TCC AAC TGC GCT TCA ACA GAA AAA ATC TAT ATC CGA
181: asp ser val gln cys glu arg lys pro ile glu val arg ser arg glu lys ser ser asn cys ala ala ser thr glu lys ile tyr ile arg 757: AAG GAC CTT CGT AGC CCA TTA ACT GCA ACT CCA ACT TTT GTA ACA GAT AGT GAA AGT ACA AGG TCA ACA GGA CTG TTA GAT TCA GGA ATG
211: lys asp leu arg ser pro leu thr ala thr pro thr phe val thr asp ser glu ser thr arg ser thr gly leu leu asp ser gly met 847: TTC ATG AAT ATT CAT CCA TCT GGA GTA AAA ACT GAG GCT GTG CTG ATG ACA TCA GAT AAG GCT GAA TGT CAG GGA GAT TTA AGT
241: phe met asn ile his pro ser gly val lys thr glu ala val leu met thr ser asp lys ala glu ser cys gln gly asp leu ser

FIG. 5B

937: ACA TTG GCC AAT GTG GTT ACA TCA TTA GCG AAT CTT TCT CAA AAT AGT AAT GAA ATG TCT ATG ATT GAA AGC
271: thr leu ala asn val val thr ser leu ala asn leu gly lys thr lys asp leu ser gln asn ser asn glu met ser met ile glu ser 1027: TTA AGC AAT GAT GAT ACC TCT TTG TGT GAA TTT CAA GAA ATG CAG ACC AAC GGT GAT GTT TCA AGG GCA TTT GAC ACT CTT GCA AAA GCA
301: leu ser asn asp asp thr ser leu cys glu phe gln glu met gln thr asn gly asp val ser arg ala phe asp thr leu ala lys ala 1117: TTG AAT CCT GGA GAG AGC ACA GCC TGC CAG AGC TCA GTA GCG GGC ATG GAA GGA AGT GTA CAC CTA ATC ACT GGA GAT TCA AGC ATA AAT
331: leu asn pro gly glu ser thr ala cys gln ser ser val ala gly met glu gly ser val his leu ile thr gly asp ser ser ile asn 1207: TAC ACC GAA AAA GAG GGG CCA CTT CTC AGC GAT CAT GTA GCT TTC AGG CTC ACC ATG CCT TCT CCT ATG CCT ATT CCT TCT TTC CAG GCT CTA GGG CAA GAA
361: tyr thr glu lys glu gly pro leu leu ser asp his val ala phe arg leu thr met pro ser pro met pro ile pro ser phe gln ala leu gly gln glu 1297: CAC TAC ATT GGG GAG TCT GCC TCC AGA CTG CTG TTC TTA TCA ATG CAC TGG GCA CTT CCT AAT GTA GCA ACT ATA
391: his tyr ile gly glu ser ala ser arg leu leu phe leu ser met his trp ala leu ser met his trp ala leu gly gln glu 

1297: CAC TAC ATT GGG GAG TCT GCC TCC AGA CTG CTG TTC TTA TCA ATG CAC TGG GCA CTT CCT ATT CCT TCT TTG ATT CCT TCT TTC CAG GCT CTA GGG CAA GAA
391: his tyr ile gly glu ser ala ser arg leu leu phe leu ser met his trp ala leu pro ile pro ser phe gln ala leu gly gln glu 1387: AAC AGC ATA TCA CTG GTG AAA GCT TAC TGG AAT GAA CTT TTT ACT CTT GGT CTT GCC CAG TGC TGG CAA GTG ATG AAT GTA GCA ACT ATA
421: asn ser ile ser leu val lys ala tyr trp asn glu leu phe thr leu gly leu ala gln cys trp gln val met asn val ala thr ile

FIG. 5C

1477: TTA GCA ACA TTT GTC AAT TGT CTT CAC AAT AGT CTT CAA CAA GCA GAG GGG TAA TCACCTTAAAATGTCATCAAAAATAGATCTAGAAGGCAGCATCA

451: leu ala thr phe val asn cys leu his asn ser leu gln gln ala glu gly

1578: CATTCCCATCTACTTATGCACTCCTACCCCTTGGTTCATGTCTTATATGCCTGTAATGCTGTAAATGGTTATAAAGCCTACTTCAGGAAAGCTATGGTTGACTAATTACTAATGGATGGTTTTAAA

1697: CATGTCCCTCTACAATAAATTAAAATCTTTCAATGTTGAATATAATGTGGAGGTGTTACCTGAGCCCCTCTCTATCTCCCCGAATTC

FIG. 5D

Human Tr-11

```
                                                        GCCACTGTCCGGTCCCCGCCCCGACCCGAGTCACCAGGCGAAACCGGTAGATC
  57:  ATG GCA ACC ATA GAA GAA ATT GCA CAT CAA ATT ATT GAA CAA CAG ATG GAG CAG ATT GTT ACA GAG CAG CAA ACT GGG CAG AAA ATC CAG
   1:  met ala thr ile glu glu ile ala his gln ile ile glu gln gln met gly ile glu val thr glu gln gln thr gly gln lys ile gln 147:  ATT GTG ACA GCA CTT GAT CAT AAT CAC GAC AAG CAG TTC ATT CTG AAA GGC TCT ACT CCA AGC GCC AAA GTC ATT CTG GCC
  31:  ile val thr ala leu asp his asn his asp lys gln phe ile leu lys gly ser thr pro ser lys val ile leu ala 237:  AGG CAA GAT TCC ACT CCG GGA AAA GTT TTC CTT ACA GAT CCA GGT GTC AAC CAG TTA TTT TTT ACC CCT GAT CTG TCT
  61:  arg gln asp ser thr pro gly lys val phe leu thr asp pro gly val asn gln leu phe phe thr pro asp leu ser 327:  GCA CAA CAC CTG CAG CTC CTA ACA GAT AAT TCT CCA GAC CAA CCA AAT AAG GTT TTT GAT CTT TGC GTA GTA TGT GGA CAC AAA GCA
  91:  ala gln his leu gln leu leu thr asp asn ser pro asp gln pro asn lys val phe asp leu cys val val cys gly asp lys ala 417:  TCA GGA CGT CAT TAT GGA GCA GTA ACT TGT GAA GGC ACT GAA GGA TTT TTT AAA AGA ATC CGA AAA AAT TTA GTA TAT TCA TGT CGA
 121:  ser gly arg his tyr gly ala val thr cys glu gly thr glu gly phe phe lys arg ile arg lys asn leu val tyr ser cys arg 507:  GGA TCA AAG GAT TGT ATT ATT AAT AAG CAC CAC CGA AAC CAC TGT CAA TAC TGC AGG TTA CAG AGA TGT ATT CGG TTT GGA ATG CAA
 151:  gly ser lys asp cys ile ile asn lys his his arg asn arg cys gln tyr cys arg leu gln arg cys ile ala phe gly met gln 597:  GAC TCT GTC CAA TGT CAA GAA AGA AAA CCC ATT GAA GTA TCA CGA GAA AAA TCT TCC AAC TGC CCT TCA ACA GAA ATC TAT ATC CGA
 181:  asp ser val gln cys gln glu arg lys pro ile glu val ser arg glu lys ser ser asn cys pro ser thr glu ile tyr ile arg 687:  AAG GAC CTT CGT ACC CCA TTA ACT GCA ACT CCA ACT TTT GTA ACA GAT AGT ACA AGA CTG TTA GAT TCA GGA ATG
 211:  lys asp leu arg ser pro leu thr ala thr pro thr phe val thr asp ser thr arg ser thr gly leu asp ser gly met
```

FIG. 6A

777: TTC ATG AAT ATT CAT CCA TCT GGA GTA AAA ACT GAG TCA GCT GTG CTG ATG ACA TCA GAT AAG CCT GAA TCA TGT CAG GGA GAT TTA AGT
241: phe met asn ile his pro ser gly val lys thr glu ser ala val leu met thr ser asp lys ala glu ser cys gln gly asp leu ser 867: ACA TTG GCC AAT GTG GTT ACA TCA TTA GCG AAT CTT GGA AAA ACT AAA GAT TCT CAA AAT AGT GAA ATG TCT ATG AGT GAA AGC
271: thr leu ala asn val val thr ser leu ala asn leu gly lys thr lys asp leu ser gln asn ser glu met ser met ile glu ser 957: TTA AGC AAT GAT GAT ACC TTG TGT GAA TTT CAA GAA ATG CAG ACC GAT GTT TCA AGG GCA TTT GAC ACT CTT GCA AAA GCA
301: leu ser asn asp asp thr ser leu cys glu phe gln glu met gln thr asp val ser arg ala phe asp thr leu ala lys ala 1047: TTG AAT CCT GAA GAG AGC ACA TCC CAG AGC ACA GCG ATG GGA GCA AGT GTA CAC CTA ATC ACT GGA GAT TCA AGC ATA AAT
331: leu asn pro glu glu ser thr ser gln ser thr ala met gly met gly ala ser val his leu ile thr gly asp ser ser ile asn 1137: TAC ACC GAA AAA GAG GGG CCA CTT CTC AGG CAT GTA GCT TTC AGC CTC ATG CCT TCT ATG CCT ATG CCT AGG TAC CTG AAT CTG
361: tyr thr glu lys glu gly pro leu leu arg his val ala phe ser leu met pro ser pro met pro arg tyr leu asn val 1227: CAC TAC ATT GGG GAG TCT GCC TCC AGA TCA AGC ATG CTG TTC TTA ATG CAC TGG CTA CTT CCT TCT TTC CAG CCT CTA GGG CAA GAA
391: his tyr ile gly glu ser ala ser arg leu leu phe leu met his trp ala leu pro ser phe gln ala leu gly gln glu 1317: AAC ACC ATA ATA TCA GTG GTG GTG AAA CTT GTC AAT TGT CAC AAT CTT TTT ACT CTT GGT CTT GCC CAG TGC TGG CAA GTG ATG AAT GTA GCA ACT ATA
421: asn ser ile ser leu val lys leu ala asn cys his asn leu phe thr leu gly leu ala gln cys trp gln val met asn val ala thr ile 1407: TTA GCA ACA TTT GTC AAT TGT CAC AAT CTT CTT CAA CAA GAT CAG AGT GAC CTT CAT TTT TTT TTA ATG GAG CAC ATC TTC
451: leu ala thr phe val asn cys leu his asn ser leu gln asn asp lys met ser thr glu arg arg lys leu met glu his ile phe 1497: AAA CTA CAG GAG TTT TGT AAC AGC ATG GTT AAC CTC ATT GAT GGA TAC GAA TAT GAT GGT TAC CTG AAG GCA ATA GTA CTC TTC AGT CCA
481: lys leu gln glu phe cys asn ser met val lys leu cys ile asp gly tyr glu tyr asp gly tyr leu lys ala ile val leu phe ser pro

FIG. 6B

```
1587: GAT CAT CCA AGC CTA GAA AAC ATG GAA AAG GCT TAT GTG GAA TTC CAA GAT TAT ATA ACC AAA ACA TAT
 511: asp his pro ser leu glu asn met glu lys ala tyr val glu phe gln asp tyr ile thr lys thr tyr 1677: CCA GAT GAC ACC AGG TTA TCC AGA CTA CTC AGA TTC CCA GCT TTA AGA CTG ATG AAT GCT ATC ACT GAA GAA TTG TTT TTC
 541: pro asp thr arg leu ser arg leu leu arg phe pro ala leu arg leu met asn ala thr ile thr glu glu leu phe phe 1767: AAA GGT CTC ATT GGC AAT ATA CGA AGT GTT ATC CCA CAT ATT TTG AAA ATG GAG CCT GCA GAT TAT AAC TCT CAA ATA ATT GGT
 571: lys gly leu ile gly asn ile arg ser val ile pro his leu lys met glu pro ala asp tyr asn ser gln ile ile gly 1857: CAC AGC ATT TGA AAACTGTGACTGCAGTGCCTGTAAACTAAACTGTTCTTTTGCCAGAACACAAGACACCTGAACTCACTGCTCTTTTGAGCATCTGAAATTTTACTTTAAA
 601: his ser ile STOP 1972: AAGTAACCAGAATCCAAGGTATTTTATTTTACCTTCCCTTAAGAATTTTTGAAGTGACTGGGCAGGCAGGCACGAGAAATAAAGAATTAAAAATGAATTCCTTTAAATGATATGAAA 2091: CACTACAAATTTATTCTTGGTGAAGATGATACCTGAAGCTGTCACCCTCTTGATTATCTAAACTAAGCGCCTCATTCTATTTTATAAACAAATAAATTAGTCTCTTTTTCTGAAAAAA

2210: AAAAAAAACCC
```

| | | | | | | | | | | | | | | |
|---|---|---|---|---|---|---|---|---|---|---|---|---|---|---|
| h-GR 463 | Lys | Ile | Arg | Lys | Asn | Cys | Pro | Ala | Cys | Arg | Tyr | Arg | Lys | Cys | Leu | Gln | Ala | Gly | Met | Asn | Leu | Glu | Ala |
| h-MR 649 | Lys | Ile | Arg | Arg | Lys | Asn | Cys | Pro | Ala | Cys | Arg | Leu | Arg | Lys | Cys | Leu | Gln | Ala | Gly | Met | Asn | Leu | Gly | Ala |
| h-PR 613 | Lys | Ile | Arg | Arg | Lys | Asn | Cys | Pro | Ala | Cys | Arg | Leu | Arg | Lys | Cys | Cys | Gln | Ala | Gly | Met | Val | Leu | Gly | Gly |
| h-AR | Lys | Phe | Arg | Arg | Lys | Asn | Cys | Pro | Ser | Cys | Arg | Leu | Arg | Lys | Cys | Tyr | Glu | Ala | Gly | Met | Thr | Leu | Gly | Ala |
| r-AR | Lys | Phe | Arg | Arg | Lys | Asn | Cys | Pro | Ser | Cys | Arg | Leu | Arg | Lys | Cys | Tyr | Glu | Ala | Gly | Met | Thr | Leu | Gly | Ala |
| h-ER 231 | Lys | Asn | Arg | Arg | Lys | Ser | Cys | Gln | Ala | Cys | Arg | Leu | Arg | Lys | Cys | Tyr | Glu | Val | Gly | Met | Met | Lys | Gly | Gly |
| h-TR2 | Lys | His | Asn | Arg | Gln | Cys | Gln | Tyr | Cys | Arg | Leu | Gln | Lys | Cys | Ile | Ala | Phe | Gly | Met | Lys | Gln | Asp | Cys |
| v-erbA86 | Lys | Ile | Thr | Arg | Asn | Gln | Cys | Gln | Leu | Cys | Arg | Phe | Lys | Lys | Cys | Ile | Ser | Val | Gly | Met | Ala | Met | Asp | Leu |
| c-VDR | Lys | Asp | Asn | Arg | Arg | His | Cys | Gln | Ala | Cys | Arg | Leu | Arg | Arg | Cys | Val | Asp | Ile | Gly | Met | Met | Lys |

FIG. 7B

```
        170         180         190         200         210         220         230         240         250
ATG CAA ACA CAA AAA CCG ACT CTC GAA CTG CTA ACC TGC GAA GCC GCT TAT CCC GAC AAT CCC ACC CTT TTT CAC CAG TTG TGT GGG
MET GLN THR GLN LYS PRO THR LEU GLU LEU LEU THR CYS GLU GLY ALA TYR ARG ASP ASN PRO THR ALA LEU PHE HIS GLN LEU CYS GLY
 1                                         10                                          20                          30

260         270         280         290         300         310         320         330         340
GAT CGT CCG GCA ACG CTG CTG CTG GAA TCC GCA GAT ATC GAC AAA GAT GAT TTA AAA ACC CTG CTG CTG GTA GAC GCG CTG CCC
ASP ARG PRO ALA THR LEU LEU LEU GLU SER ALA ASP ILE ASP LYS ASP ASP LEU LYS THR LEU LEU LEU VAL ASP ALA LEU ARG
                        40                                          50                                          60

350         360         370         380         390         400         410         420         430
ATT ACA GCT TTA GGT GAC ACT GTC ACA ATC CAG GCA CTT TCC GGC AAC GGC GAA CCC CTC CTG GCA CTA CTG GAT AAC GCC CTG CCT GCG
ILE THR ALA LEU GLY ASP THR VAL THR ILE GLN ALA LEU SER GLY ASN GLY GLU ALA LEU LEU ALA LEU LEU ASP ASN ALA LEU PRO ALA
                        70                                          80                                          90

440         450         460         470         480         490         500         510         520
GGT GTG GAA AGT GAA CAA TCA CCA AAC TGC CGT GTG CTG CCC CCT GTC CTG GAT GAA GAC CCA CTG CTG TTA TGC TTC
GLY VAL GLU SER GLU GLN SER PRO ASN CYS ARG VAL LEU ARG PHE PRO PRO VAL LEU ASP GLU ASP ALA ARG LEU CYS SER
                       100                                         110                                         120

530         540         550         560         570         580         590         600         610
CTT TCG GTT TTT GAC GCT GCT TTA TTG CAG AAT CTG TTG CAG AAT CTG TTG CAG CTG AAT CTA AAT GTA CCG AAG GAA GGA GAA CCC ATG TTC TTC AGC GGC CTG TTC
LEU SER VAL PHE ASP ALA ALA PHE ALA ARG LEU LEU GLN ASN LEU LEU GLN ASN VAL PRO LYS GLU GLU ARG GLU ALA MET PHE PHE SER GLY LEU PHE
                       130                                         140                                         150
```

FIG. 9A

TCT TAT GAC CTT GTG GCG GGA TTT GAA GAT TTA CCG CAA CTG TCA CCG GAA AAT AAC TGC CCT GAT TTC TGT TTT TAT CTC GCT GAA ACG
SER TYR ASP LEU VAL ALA GLY PHE GLU ASP LEU PRO GLN LEU SER PRO GLU ASN ASN CYS PRO ASP PHE CYS PHE TYR LEU ALA GLU THR
              160                              170                              180

CTG ATG GTG ATT GAC CAT CAG AAA AAA ACC CGT CAG GCC ATT CAG CCG AGC ACC CTG TTT GCT CCG AAT GAA GAA AAA CAA CTC ACT GCT
LEU MET VAL ILE ASP HIS GLN LYS LYS THR ARG GLN ALA ILE GLN ALA SER THR LEU PHE ALA PRO ASN GLU GLU LYS GLN LEU THR ALA
              190                              200                              210

CGC CTG AAC GAA CTA CGT CAG CAA CTG ACC GAA GCC GCG CCG CCG CTG CCA GTG GTT TCC GTG CAT ATG CGT GAA TGT AAT CAG
ARG LEU ASN GLU LEU ARG GLN GLN LEU THR GLU ALA ALA PRO PRO LEU PRO VAL VAL SER VAL PRO HIS MET ARG CYS ASN GLN
              220                              230                              240

AGC GAT GAA GAG TTC GGT GGC GTA GTG TTG CAA AAA GCG ATT CCG GCT GGA GAA ATT TTC CAG GTG GTG CCA TCT CCC GGT TTC
SER ASP GLU GLU PHE GLY GLY VAL VAL LEU ARG LEU VAL ARG ALA ILE ARG ALA GLY GLU ILE PHE GLN VAL VAL PRO SER ARG ARG PHE
              250                              260                              270

TCT CTG CCC TGC TCA CCG CTG GCG CCC TAT TAC GTG CTG AAA AAG AGT AAT CCC AGC CCG TAC ATG TTT TTT ATG CAG GAT AAT GAT
SER LEU PRO CYS SER PRO LEU ALA PRO TYR TYR VAL LEU LYS LYS SER ASN PRO SER PRO TYR MET PHE PHE MET GLN ASP ASN ASP
              280                              290                              300

FIG. 9B

```
1070      1080      1090      1100      1110      1120      1130
TTC ACC CTA TTT GGC GCG TCG CCG GAA AGC TCG CTC AAG TAT GAT GCC ACC CCG CAG ATT GAG ATC
PHE THR LEU PHE GLY ALA SER PRO GLU SER SER LEU LYS TYR ASP ALA THR PRO GLN ILE GLU ILE
                              310                                    320
```

6 amino acid linker

CCC CGG AAT TCG AGC TCG
Pro Arg Asn Ser Ser Ser

FIG. 9C

GGGACACTTGAACTGCCGTCTCTCTACAAGTCCGGAGCACAGAGGTCCGACTACTACAACTTT
GlyThrLeuGluLeuProSerThrLeuSerLeuTyrLysSerGlyAlaAlaLeuAspGluAlaAlaAlaTyrGlnSerArgAspTyrTyrAsnPhe

CCCACTCGCCTCTGCCCAGCACCCCCTCGCCATCCCACCTCCCCCCCCCCCCCCCCCAGTCCCC
ProLeuAlaLeuAlaGlyProProProProProHisAlaArgIleLysLeuGluAsnProLeuAspTyrSerAlaTrpAlaAlaAlaAlaGlnCysArg

TATGGGAGACCTCGCCAGCCTCCATCGATGCCAGTCTCTGGAGACCCTGGTCAGGGACCCCTGAGGGAGGTCTCCTCATCGTCCCTTCCCTCTACAGGGAAGACCCAGTTGTAT
TyrGlyAspLeuAlaSerLeuHisGlyAlaAlaGlyProGlySerProSerAlaAlaAlaSerSerSerTrpHisThrLeuPheThrAlaGluGluGlyGlnLeuTyr

GGACGTGTGGTGGTGGGTGGCGGCGGCGGCGGCGGCGGCGGCGGCGGCGGCGGCGGCGGCGGCGGCGGCGGCGGCGAAGCTGTAGCCCCCTAGGGTAC
GlyProCysGlyGlyGlyGlyGlyGlyGlyGlyGlyGlyGlyGlyGlyGlyGlyGlyGlyGlyGlyGlyGlyGlyGlyGlyGlyGlyAlaAlaValAlaProTyrGlyTyr

ACTCGGCCCCTCAGGGCTGCGGCGCAGAAAGGACTTCACGGCACCTTGCGGCATGGTGACCAAGTCGCCTATCCAGTCCCACTGTGTCAAAGGAA
ThrArgProProGlnGlyLeuAlaGlyValGlnGluSerAspPheThrAlaProGlyMetValSerArgValProTyrProSerProThrCysValLysSerGlu

FIG. 9D

ATGGCCCCTGGATGATAGCTACTCCGGACCTTACGGGCAGACATGGTTTGGAGACTGCAGGACCATGTTTGCCCATTGACTATTACTTTCCACCCCAGAAGACCTGCCTGATCTGT
MetGlyProTrpMetAspSerTyrSerGlyProTyrGlyAspMetArgLeuGluThrAlaArgAspHisValLeuProIleAspTyrTyrPheProProGlnLysThrCysLeuIleCys

GGAGATGAACCTTCTGGGTGTCACTATGGACCT
GlyAspGluAlaSerGlyCysHisTyrGlyAla ⎤
  CGC CCG GGG ATC CTC TAG
  Arg Pro Gly Ile Leu STOP    5 amino acid linker Total amino acid:    323 + 6 + 242 + 5 = 576

FIG. 9E

```
     170         180         190         200         210         220         230         240         250
ATG CAA ACA CAA AAA CCG ACT CTC GAA CTG CTA ACC TGC GAA GGC GCT TAT CGC AAT CCC ACC GCG CTT TTT CAC CAG TTG TGT GGG
MET GLN THR GLN LYS PRO THR LEU GLU LEU LEU THR CYS GLU GLY ALA TYR ARG ASP ASN PRO THR ALA LEU PHE HIS GLN LEU CYS GLY
 1                              10                              20                              30

260         270         280         290         300         310         320         330         340
GAT CGT CCG GCA AGG CTG CTG CTG CTG GAA CTG CTG CTG CCA GAT ATC GAC AGC GCA GAT TTA AAA AGC CTG CTG CTG GTA GAC AGT GGG CTG CGC
ASP ARG PRO ALA ARG LEU LEU LEU LEU GLU LEU LEU LEU PRO ASP ILE ASP SER ALA ASP LEU LYS SER LEU LEU LEU VAL ASP SER GLY LEU ARG
                                40                              50                              60

350         360         370         380         390         400         410         420         430
ATT ACA GCT TTA GAC ACT GTC ACA ATC CAG GCA CTT TCC CGC AAC GGG GAA GCC CTC CTG GCA CTA CTG GAT AAC GCC CTG CCT GCG
ILE THR ALA LEU ASP THR VAL THR ILE GLN ALA LEU SER ARG ASN GLY GLU ALA LEU LEU ALA LEU LEU ASP ASN ALA LEU PRO ALA
                                70                              80                              90

440         450         460         470         480         490         500         510         520
GGT GTG GAA AGT GAA CAA TCA CAA AAC TGC CGT GTG CTG CCC TTC CCC GTC CTG AGT CCA CTG GAT GAA GAC CCC TTA TGC TCC
GLY VAL GLU SER GLU GLN SER GLN ASN CYS ARG VAL LEU ARG PHE PRO VAL LEU ASP GLU ASP ALA ARG LEU CYS SER
                               100                             110                             120

530         540         550         560         570         580         590         600         610
CTT TCG GTT TTT GAC GCT TTA CGT TTA TTG CAG AAT CTG TTG AAT CTG TTG CAG AAT GTA CCG AAG GAA GAA CGA GAA ATG TTC TTC AGC GGC CTG TTC
LEU SER VAL PHE ASP ALA PHE ARG LEU LEU GLN ASN LEU LEU ASN VAL PRO LYS GLU GLU ARG GLU ALA MET PHE PHE SER GLY LEU PHE
                               130                             140                                                 130
```

FIG. 10A

```
                 620           630           640           650           660           670           680           690           700
         TCT TAT GAC CTT GTG GCG GGA TTT GAA GAT TTA CCG CAA CTG TCA GGG GAA AAT AAC TCC CCT GAT TTC TGT TAT CTC GCT GAA ACG
         SER TYR ASP LEU VAL ALA GLY PHE GLU ASP LEU PRO GLN LEU SER GLY GLU ASN ASN CYS PRO ASP PHE CYS TYR LEU ALA GLU THR
                             160                           170                           180

710           720           730           740           750           760           770           780           790
         CTG ATG GTG ATT GAC GGT CAG CAA AAA ACC CGT ATT CAG GCC AGC ACG CTG TTT GCT CCG AAT GAA GAA GAA AAA CAA CGT CTC ACT GCT
         LEU MET VAL ILE ASP HIS GLN LYS SER THR ARG ILE GLN ALA SER LEU PHE ALA PRO ASN GLU GLU GLU LYS GLN ARG LEU THR ALA
                             190                           200                           210

800           810           820           830           840           850           860           870           880
         CGC CTG AAC GAA CTA CGT CAG CAA CTG AAC GAG CTG CCA GTT TCC GTG CAT ATG CGT TGT GAA TGT GAA CGT TGT GAA TGT CGT AAT CAG
         ARG LEU ASN GLU LEU ARG GLN GLN LEU ASN GLU LEU PRO VAL SER VAL PRO HIS MET ARG CYS GLU CYS ASN GLN
                             220                           230                           240

890           900           910           920           930           940           950           960           970
         AGC GAT GAA GAG TTC GGT GGC GTA GTG CGT TTG CAA AAA GCG ATT CGC GGA GAA ATT TTC CAG GTG GTG CCA TCT CGC CGT TTC
         SER ASP GLU GLU PHE GLY GLY VAL VAL ARG LEU LEU GLN LYS ALA ILE ARG ALA GLY GLU ILE PHE GLN VAL VAL PRO SER ARG ARG PHE
                             250                           260                           270

980           990           1000          1010          1020          1030          1040          1050          1060
         TCT CTG CCC TCC CCG CTG CCG TCA CCG CTG CCC TAT TAC CTG GTG AAA AAG AGT AAT CCC AGC CCC TAC ATG TTT ATG CAG GAT AAT GAT
         SER LEU PRO CYS PRO LEU PRO SER PRO LEU ALA TYR TYR VAL LEU LYS LYS SER ASN PRO SER PRO TYR MET PHE MET GLN ASP ASN ASP
                             280                           290                           300
```

FIG. 10B

```
      1070      1080      1090      1100      1110      1120      1130
TTC ACC CTA TTT GGC CCG TCG CCG GAA AGC TCG CTC AAG TAT GAT GCC ACC ACC CGC CAG ATT GAG ATC
PHE THR LEU PHE GLY ALA SER PRO GLU SER SER LEU LYS TYR ASP ALA THR SER ARG GLN ILE GLU ILE
                              310                                        320
```

11 amino acid linker

```
CCC GGG CGA GCT CGA ATT CGA GCT CGC CCG GGG
Pro Gly Arg Ala Arg Ile Arg Ala Arg Pro Gly
```

FIG. 10C

ATC TGT GGA GAT GAA GCT TCT GGT TGT CAC TAC GGA GCT CTC ACT TGT GCC AGC 561
ils cys gly asp glu ala ser gly cys his tyr gly ala leu thr cys gly ser TGC AAG GTC TTC TTC AAA AGA GCT CCG GAA GCG AAA CAG AAG TAT CTA TGT GCC AGA AAT GAT AAA TTT CGG AGG 591
cys lys val phe phe lys arg ala ala glu gly lys gln lys tyr leu cys ala ser arg asn asp cys thr ile asp lys phe arg arg AAA AAT TGT CCA TGG TGT CGT CTC CGG AAA TGT TAT GAA GCA GGG ATG ACT CTG GGA GCT CGT AAG CTG AAG AAA CTT GGA AAT CTC AAA 621
lys asn cys pro ser cys arg leu arg lys cys tyr glu ala gly met thr leu gly ala arg lys leu lys leu gly asn leu lys CTA CAG GAA GGA GAA AAC TCC AGT GCT GGT AGC CCC ACT GAG GAC CCA TCC CAG AAG ATG GTA TCA CAC ATT GAA GGC TAT GAA 651
leu glu glu gly glu asn ser ser ala gly ser pro thr glu asp pro ser gln lys met val ser his ile glu gly tyr glu TGT CAA CCT ATC TTT CTT AAT GTC CTG GAA GCC ATT GAG GAG CAG GTT GTG CCA CAT GAC GTC AAG AAC CAG CCT GAT TCC TTT GCT 681
cys gln pro ile phe leu asn val leu glu ala ile glu glu gln val val pro his asp val lys asn gln pro asp ser phe ala GCC TTG TTA TCT AGT CTC AAC GAG CTT GTA CAT GTG GTC AAG TGG GCC AAG GCC TTG CCT GCC TTC CCC AAC TTG 711
ala leu leu ser ser leu asn glu leu val his val val lys trp ala lys ala leu pro ala phe arg asn leu CAT GTG GAT GAC CAG ATG GCA GTC ATT CAG TAT TCC ATG ATG GAC CTG GTA TTT GCC ATG GGT TGG CGG TCC TTC ACT AAT GTC AAC 741
his val asp asp gln met ala val ile gln tyr ser met met gly leu val phe ala met gly trp arg ser phe thr asn val asn TCT AGG ATG CTC TAC TTT GCA CCT GAC CTG GTT TTC AAT GAG TAT CGA ATG CAC AAG TCT CGA ATG TAC AGC CAG TGC GTG AGG ATG AGG 771
ser arg met leu tyr phe ala pro asp leu val phe asn glu tyr arg met his lys ser arg met tyr ser gln cys val arg met arg

FIG. 10D

CAC CTT TCT CAA GAG TTT GGA TGG CTC CAG ATA ACC CCC CAG GAA TTC CTG TGC ATG AAA GCA CTG CTA CTC TTC ACC ATT ATT CCA GTG 801
his leu ser gln glu phe gly trp leu gln ile thr pro gln glu phe leu cys met lys ala leu leu leu phe ser ile ile pro val GAT GGG CTG AAA AAT CAA AAT TTC TTT GAT GAA CTT GAT GAA CTT GAT
asp gly leu lys asn gln lys phe phe asp glu leu asp glu leu asp AAG TAC ATC AAG GAA CTT GAT
lys tyr ile lys glu leu asp CCT CTA GAG TCG ACC TGC AGC CCA AGC TTA TCG ATG ATA AGC TGT CAA ACA TGA
Pro Leu Glu Ser Thr Cys Ser Pro Ser Leu Ser Met Ile Ser Cys Gln Thr 17 amino acid linker Total amino acids: 323 + 11 + 279 + 17 = 630

FIG. 10E

323 amino acids from TRP E protein

```
       170         180         190         200         210         220         230         240         250
ATG CAA ACA CAA AAA CCG ACT CTC GAA CTG CTA ACC TGC GCT TAT CCC GGT GGA TYR CCG CTT TTT CAC CAG TTG TGT GGG
MET GLN THR GLN LYS PRO THR LEU GLU LEU LEU THR CYS GLU GLY ALA TYR ARG ASP ASN PRO THR ALA LEU PHE HIS GLN LEU CYS GLY
 1                                              10                                          20                       30

260         270         280         290         300         310         320         330         340
GAT CGT CCG GCA ACG CTG CTG CTG GAA TCC CCA GAT ATC GAC ACC AGC AAA GAT TTA AAA AGC CTG CTG CTG GTA GAC AGT GCG CTG CCC
ASP ARG PRO ALA THR LEU LEU LEU GLU SER PRO ASP ILE ASP THR SER LYS ASP LEU LYS SER LEU LEU LEU VAL ASP SER ALA LEU ARG
                              40                                          50                                          60

350         360         370         380         390         400         410         420         430
ATT ACA GCT TTA GGT GAC ACT GTC ACA ATC CAG GCA CTT TCC GGC AAC CGC CTG CTG GCA CTA CTG GAT AAC GCC CTG CCT GCG
ILE THR ALA LEU GLY ASP THR VAL THR ILE GLN ALA LEU SER GLY ASN ARG LEU LEU ALA LEU LEU ASP ASN ALA LEU PRO ALA
                              70                                          80                                          90

440         450         460         470         480         490         500         510         520
GGT GTG GAA AGT GAA CAA TCA CCA AAC TGC CGT GTG CTG CGG TTC CCC CCT GTC CTG AGT CCA CTG GAT GAC CTG CCA TTA TGC TCC
GLY VAL GLU SER GLU GLN SER PRO ASN CYS ARG VAL LEU ARG PHE PRO PRO VAL SER PRO LEU ASP ASP LEU PRO LEU CYS SER
                             100                                         110                                         120

530         540         550         560         570         580         590         600         610
CTT TCG GTT TTT GAC GCT GCT TTC CGT TTA CGG AAT CTG TTG CAG AAT GTA CCG AAG GAA GAA GAA CGA GCC ATG TTC TTC AGC CTG TTC
LEU SER VAL PHE ASP ALA ALA PHE ARG LEU ARG ASN LEU LEU GLN ASN VAL PRO LYS GLU ARG GLU ALA MET PHE PHE SER GLY LEU PHE
                             130                                         140                                         150
```

FIG. 11A

```
 620        630         640         650         660         670        680         690         700
TCT TAT GAC CTT GTG GCG GGA TTT GAA GAT TTA CCG CAA CTG TCA GCG GAA AAT TGC CCT GAT TTC TGT TTT TAT CTC GCT SAA ACG
SER TYR ASP LEU VAL ALA GLY PHE GLU ASP LEU PRO GLN LEU SER ALA GLU ASN CYS PRO ASP PHE CYS PHE TYR LEU ALA GLU THR
                    160                                      170                                      180

710         720         730         740         750         760         770         780         790
CTG ATG GTG ATT GAC CAT CAG AAA AAA AGC ACC CGT ATT CAG GCC ACC CTG TTT GCT CCG AAT GAA GAA AAA CAA CGT CTC ACT GCT
LEU MET VAL ILE ASP HIS GLN LYS LYS SER THR ARG ILE GLN ALA THR LEU PHE ALA PRO ASN GLU GLU LYS GLN ARG LEU THR ALA
                    190                                      200                                      210

800         810         820         830         840         850         860         870         880
GCC AAC GAA CTA CGT CAG CAA CTG ACC CTG ACC GCC GCG CCG GTT TCC GTG CCG CAT ATG CGT TGT GAA TGT AAT CAG
ALA ASN GLU LEU ARG GLN GLN LEU THR LEU THR ALA ALA PRO LEU PRO VAL VAL SER VAL PRO HIS MET ARG CYS GLU CYS ASN GLN
                    220                                      230                                      240

890         900         910         920         930         940         950         960         970
AGC GAT GAA GAG TTC GGT GGC GTA GTG CGT GGT TTG TTG CAA AAA GCG ATT GGA GAA ATT TTC GCT GGA GCA ATC TTC CAG GTG GTG TTC
SER ASP GLU GLU PHE GLY GLY VAL VAL ARG GLY LEU LEU GLN LYS ALA ILE ALA ILE PHE GLN VAL VAL PHE
                    250                                      260                                      270

980         990        1000        1010        1020        1030        1040        1050        1060
TCT CTG CCC TGC CCG TCA CCG CTG GCG GCC TAT TAC STS CTS AAA AAG AGT AAT CCC AGC CCG TAC ATG TTT TTT ATG CAG GAT AAT GAT
SER LEU PRO CYS PRO SER PRO LEU ALA ALA TYR TYR VAL LEU LYS LYS SER ASN PRO SER ARG TYR MET PHE PHE MET GLN ASP ASN ASP
                    280                                      290                                      300
```

FIG. 11B

2 amino acid linker

GAA TTC CTG TGC ATG AAA GCA CTG CTA CTC TTC ACC ATT ATT CCA GTG    801
glu phe leu cys met lys ala leu leu leu phe ser ile ile pro val GGT GGT CTG AAA AAT CAA AAA TTC TTT GAT GAA CTT CGA ATG AAC TAC ATC AAG GAA CTT GAT CCC ATC CCC AAA AGA AAA AAT    831
asp gly leu lys asn gln lys phe phe asp glu leu arg met asn tyr ile lys glu leu asp pro ile pro lys arg lys asn CCC ACA TCC TGC TCA AAG CTC TAC CAG CTC ACC AAG CTC CTG GAT TCT GTG CAG CCT ATT GCA AGA GAG CTG CAT CAA TTC ACT TTT    861
pro thr ser cys ser lys leu tyr gln leu thr lys leu leu asp ser val gln pro ile ala arg glu leu his gln phe thr phe GAC CTG CTA ATC AAG TCC CAT ATG GTG GAC GTT CCT GAA ATG GCA ATG ATG GAG ATC ATC TCT GTG CAA GTG CCC AAG ATC CTT TCT    891
asp leu leu ile lys ser his met val asp val pro glu met ala met met glu ile ile ser val gln val pro lys ile leu ser GGG AAA GTC AAG CCC ATC TAT TTC CAC ACA CAG TGA
gly lys val lys pro ile tyr phe his thr gln ***

Total amino acids: 323 + 2 + 177 = 442

FIG. 11D

DNA BINDING PROTEINS INCLUDING ANDROGEN RECEPTOR

The United States Government may have certain rights in the present invention pursuant to grant number NIH-DDKD DK 37694.

CROSS-REFERENCE TO RELATED APPLICATIONS

The present invention is a continuation-in-part of co-pending U.S. patent application Ser. No. 07/438,775, filed Nov. 17, 1989 now abandoned; which in turn is a continuation-in-part of U.S. patent application Ser. No. 07/253,807, filed Oct. 5, 1988 now abandoned; which in turn is a continuation-in-part of U.S. patent application Ser. No. 07/176,107, filed Mar. 30, 1988, now abandoned.

BACKGROUND OF THE INVENTION

The present invention relates generally to DNA binding regulatory proteins and more particularly to DNA sequences encoding androgen receptor protein and novel DNA binding proteins designated TR2, to the polypeptide products of recombinant expression of these DNA sequences, to peptides whose sequences are based on amino acid sequences deduced from these DNA sequences, to antibodies specific for such proteins and peptides, and to procedures for detection and quantification of such proteins and nucleic acids related thereto.

There are five major classes of steroid hormones: progestins, glucocorticoids, mineralocorticoids, androgens, and estrogens. Receptor proteins, each specific for asteroid hormone, are distributed in a tissue specific fashion and in target cells, steroid hormones can form specific complexes with corresponding intracellular receptors. [Jensen, et al., *Proc. Nat'l. Acad. Sci. (USA)*, 59:632 (1968); Gorski, et al., *Ann. Rev. Physiol.*, 38:425–450 (1976); and Liao, et al., page 633 in *Biochemistry of Hormones*, H. L. J. Makin, ed. (Blackwell Sci. Publ. Oxford, 1984)]. The hormonal regulation of gene expression appears to involve interaction of steroid receptor complexes with certain segments of genomes and modulation of specific gene transcription. See, e.g., Ringold, *Ann. Rev. Pharmacol. Toxicol.*, 25:529 (1985); and Yamamoto, *Ann. Rev. Genet.*, 19:209 (1985). Many of the primary effects of hormones involve increased transcription of a subset of genes in specific cell types.

The successful cloning of e.g., cDNAs coding for various steroid receptors has allowed the structural and functional analysis of different steroid receptor domains involved in steroid and DNA binding. See, e.g., Hollenberg, et al., *Nature (London)*, 318:635 (1985); Miesfeld, et al., *Cell*, 46:389 (1986); Danielsen, et al., *EMBO J.*, 5:2513 (1986); Greene, et al., *Science*, 231:1150 (1986); Green, et al., *Nature (London)*, 320:134 (1986); Krust, et al., *EMBO J.*, 5:891 (1986); Loosfelt, et al., *Proc. Nat'l. Acad. Sci. (USA)*, 83:9045 (1986); Conneely, et al., *Science*, 233:767 (1987); Law, et al., *Proc. Nat'l. Acad. Sci. (USA)*, 84:2877 (1987); Misrahi, et al., *Biochem. Biophys. Res. Commun.*, 143:740 (1987); Arriza, et al., *Science*, 237:268 (1987); Sap, et al., *Nature (London)*, 324:635 (1986); Weinberger, et al., *Nature (London)*, 318:641 (1986); Benbrook, et al., *Science*, 238:788 (1987); and Evans, *Science*, 240:889 (1988).

Androgens, such as testosterone, are responsible for the development of male secondary sex characteristics and are synthesized primarily in testis. Cloning of a cDNA for androgen receptor (AR) has been difficult because, until recently, monospecific antibodies against AR have not been available for screening cDNA libraries. An abstract by Govindan, et al., *J. Endocrinol. Invest.*, 10 (Suppl. 2) (1987), reported the isolation of cDNA clones encoding human androgen receptor isolated from a human testis λgt-11 cDNA library using synthetic oligonucleotides homologous to human glucocorticoid, estradiol, and progesterone receptors as probes. The expressed protein reportedly bound tritium-labelled DHT (dihydrotestosterone) with high affinity and specificity. However, no nucleotide or amino acid sequence analysis was provided for full length androgen receptors, nor was any description provided concerning isolation of the full length putative androgen receptor clones.

Recently, Chang, C., et al., *Science*, 240:324 (Apr. 15, 1988), co-authored by the inventors herein, described cDNAs encoding androgen receptors obtained from human testis and rat ventral prostrate cDNA libraries. These cDNAs for human and rat androgen receptor were reported to be long enough to code for 94 kDa and 76 kDa receptors. The molecular weights were derived with the assistance of a software program known as: DNA Inspector II (Textco West Lebanon, New Hampshire) open reading frame analysis. With a new DNA Inspector IIe program, hAR (918 amino acids) has an estimated molecular weight 98,608 and rAR (902 amino acids) has a molecular weight of 98,133. Therefore, the reported "94 kDa" AR is now termed "98 kDa" AR; and the hAR or rAR polypeptides, from the second ATG/Met, reported as "76 kDa" are now termed "79 kDa". See also, Chang, C., et al., *Proc. Nat'l. Acad. Sci. (USA)*, 85:7211 (Oct. 5, 1988) also co-authored by the inventors herein.

In contrast, Lubahn, D., et al., *Science*, 240:327 (1988), using libraries from human epididymis and cultured human foreskin fibroblasts obtained a human cDNA which was expressed in monkey kidney (COS) cells to yield a protein, present in the cytosol, capable of binding androgens. This cDNA, however, was only sufficient to-code for a receptor having an estimated molecular weight of 41,000. Therefore, the cDNA obtained only coded for a portion of AR.

Of interest to the present invention is Young, et al., *Endocrinol.*, 123:601 (1988), wherein the production of anti-AR monoclonal antibodies was reported. Anti-AR autoantibodies were identified in the sera of prostate cancer patients, as described in Liao, S., et al., *Proc. Nat'l. Acad. Sci. (USA)*, 82:8345 (1984) (one of the co-inventors herein), and were characterized with respect to their titer, affinity, and specificity. Subsequently, lymphocytes from the blood of those patients having high antibody titers were isolated, transformed with Epstein-Barr Virus (EBV), and cloned for anti-AR monoclonal antibody production. These monoclonal antibodies were found to interact with androgen receptors from rat prostate. An attempt to scale-up antibody production resulted in a decline of antibody secretion. It is not uncommon for transformed B-cells to be more unstable than hybridoma cells. Kozbor, et al., *Eur. J. Immunol.*, 14, 23 (1984). Because of the instability associated with such cell lines, an alternate source of monoclonal antibodies is preferred.

There thus exists a need in the art for information concerning the primary structural conformation of androgen receptor protein and other DNA binding proteins such as might be provided by knowledge of human and other mammalian DNA sequences encoding the same. Availability of such DNA sequences would make possible the application of recombinant methods to the large scale production of the proteins in procaryotic and eukaryotic host cells, as well as DNA-DNA, DNA-RNA, and RNA-RNA hybridization procedures for the detection, quantification and/or isolation of nucleic acids associated with the proteins. Possession of androgen receptor and related DNA-binding proteins and/or knowledge of the amino acid sequences of the same would make possible, in turn, the development of monoclonal and polyclonal antibodies thereto (including antibodies to protein fragments or synthetic peptides modeled thereon) for the use in immunological methods for the detection and quantification of the proteins in fluid and tissue samples as well as for tissue specific delivery of substances such as labels and therapeutic agents to cells expressing the proteins.

BRIEF SUMMARY OF THE INVENTION

The present invention provides novel purified and isolated DNA sequences encoding androgen receptor protein and a structurally related protein, designated TR2 protein, which also has DNA binding (and hence DNA replication or transcription regulatory) capacity. In presently preferred forms, novel DNA sequences comprise cDNA sequences encoding human and rat androgen receptor and human TR2 protein. Alternate DNA forms such as genomic DNA, and DNA prepared by partial or total chemical synthesis from nucleotides as well as DNA with deletions or mutations, is also within the contemplation of the invention.

Association of DNA sequences provided by the invention with homologous or heterologous species expression control DNA sequences, such as promoters, operators, regulators and the like, allows for in vivo and in vitro transcription to form messenger RNA which, in turn, is susceptible to translation to provide androgen receptor and TR2 proteins, and related poly- and oligo-peptides in large quantities. In a presently preferred DNA expression system of the invention, AR and TR2 encoding DNA is operatively associated with a viral (T7) regulatory (promoter) DNA sequence allowing for in vitro transcription and translation in a cell free system to provide, e.g., a 79 kD and 98 kD human androgen receptor (hAR) protein, 79 kD and 98 kD rat androgen receptor (rAR) protein and smaller forms of these proteins; as well as TR2 protein, including 20 kD, 52 kD, and 67 kD species.

Incorporation of DNA sequences into procaryotic and eucaryotic host cells by standard transformation and transfection processes, potentially involving suitable viral and circular DNA plasmid vectors, is also within the contemplation of the invention and is expected to provide useful proteins in quantities heretofore unavailable from natural sources. Systems provided by the invention included transformed E. coli DH5α cells, deposited Jan. 25, 1989, with the American Type Culture Collection, 12301 Parklawn Drive, Rockville, Md. 20852 in accordance with the U.S. Patent and Trademark Office's requirements for microorganism deposits, and designated EC-hAR3600 under A.T.C.C. Accession No. 67879; EC-rAR 2830, A.T.C.C. No. 67878; EC-TR2-5, A.T.C.C. No. 67877; and EC TR2-7, A.T.C.C. No. 67876; as well as transformed E. coli DH5α cells, deposited Nov. 14, 1989 and designated EC TR2-11 under A.T.C.C. No. 68173. The above deposits have been made in accordance with the terms of the Budapest Treaty on the International Recognition of the Deposit of Microorganisms for the Purposes of Patent Procedure. In accordance with the terms of the Budapest Treaty: (a) those deposits will be made accessible to the Commissioner upon request during the pendency of this application, (b) all restrictions to access by the public of those deposits will be irrevocably removed upon granting of the patent, (c) those deposits will be maintained in a public depository for a period of thirty years or five years after the last request, or for the effective life of the patent, whichever is longer, and (d) those deposits will be replaced if they should ever become inviable. Use of mammalian host cells is expected to provide for such post-translational modifications (e.g., truncation, glycosylation, and tyrosine, serine or threonine phosphorylation) as may be needed to confer optimal biological activity on recombinant expression products of the invention.

Novel protein products of the invention include polypeptides having the primary structural conformation (i.e., amino acid sequence) of AR and TR2 proteins as well as peptide fragments thereof and synthetic peptides assembled to be duplicative of amino acid sequences thereof. Proteins, protein fragments, and synthetic peptides of the invention are projected to have numerous uses including therapeutic, diagnostic and prognostic uses and will provide the basis for preparation of monoclonal and polyclonal antibodies specifically immunoreactive with AR and TR2 proteins. Preferred protein fragments and synthetic peptides include those duplicating regions of AR and TR2 proteins which are not involved in DNA binding functions and the most preferred are those which share at least one antigenic epitope with AR and TR2 proteins.

Also provided by the present invention are polyclonal and monoclonal antibodies characterized by their ability to bind with high immunospecificity to AR and TR2 proteins and to their fragments and peptides, recognizing unique epitopes which are not common to other proteins especially DNA binding proteins.

Illustratively provided according to the present invention are monoclonal antibodies, designated AN1-6, AN1-7, AN1-15; and produced by hybridoma cell lines designated H-AN1-6, H-AN1-7, H-AN1-15; deposited Jan. 25, 1989, under Accession Nos. HB 10,000; HB 9,999; and HB 10,001, respectively, with the American Type Culture Collection, 12301 Parklawn Drive, Rockville, Md. 20852 in accordance with the U.S. Patent and Trademark Office's requirements for microorganism deposits. These antibodies are characterized by (a) capacity to bind androgen receptors from rat ventral prostate and synthetic peptides having sequences predicted from the structure of hAR-cDNA and rAR-cDNA; (b) specific immunological reactivity with, and capacity to reversibly immunobind to, naturally occurring and recombinant androgen receptors, in native and denatured conformations; and (c) specific immunological reactivity with, and capacity to reversibly immunobind to, proteinaceous materials including all or a substantially, immunologically significant, part of an amino acid sequence duplicative of that extant at residues 331 through 577 of hAR and corresponding amino acid sequences in rAR.

Also provided according to the present invention are monoclonal antibodies to TR2 proteins designated A-TR-2-11a. These antibodes are characterized by their capacity to bind TR2 proteins as well as synthetic peptides having sequences predicted from the structure of hTR-2-cDNA.

The monoclonal antibodies of the invention can be used for affinity purification of AR and TR-2 receptor from human or rat prostate, and other sources such as AR-rich organs and cultured cells.

Also provided by the present invention are novel procedures for the detection and/or quantification of normal, abnormal, or mutated forms of AR and TR2, as well as nucleic acids (e.g., DNA and mRNA) associated therewith. Illustratively, antibodies of the invention may be employed in known immunological procedures for quantitative detection of AR and TR2 proteins in fluid and tissue samples, of DNA sequences of the invention (particularly those having sequences encoding DNA binding proteins) that may be suitably labelled and employed for quantitative detection of mRNA encoding these proteins.

Among the multiple aspects of the present invention, therefore, is the provision of (a) novel AR and TR2-encoding DNA sequences set out in FIG. 3A, FIG. 3B, FIG. 3C, FIG. 3D, FIG. 3E, FIG. 3F, FIG. 3G, FIG. 3H, FIG. 3I, FIG. 3J, FIG. 3K and FIG. 3L, as well as (b) AR and TR2-encoding DNA sequences which hybridize thereto under hybridization conditions of the stringency equal to or greater than the conditions described herein and employed in the initial isolation of cDNAs of the invention, and (c) DNA sequences encoding the same allelic variant, or analog AR and TR2 polypeptides through use of, at least in part, degenerate codons. Correspondingly provided are viral or circular plasmid DNA vectors incorporating such DNA sequences and procaryotic and-eucaryotic host cells transformed or transfected with such DNA sequences and vectors as well as novel methods for the recombinant production of AR and TR2 proteins through cultured growth of such hosts and isolation of these proteins from the hosts or their culture media.

Preferred polypeptide products of the invention include the approximately 79 kD (starting from the second ATG/Met) and 98 kD (starting from the first ATG/Met) hAR polypeptides having the deduced amino acid sequence of 734 and 918 residues, respectively, as set out in FIG. 3A, FIG. 3B, FIG. 3C, FIG. 3D, FIG. 3E, FIG. 3F, FIG. 3G, FIG. 3H, FIG. 3I, FIG. 3J, FIG. 3K and FIG. 3L. Also preferred are the 79 kD and 98 kD rAR species polypeptides having the deduced sequence of 733 and 902 residues set out in FIG. 3A, FIG. 3B, FIG. 3C, FIG. 3D, FIG. 3E, FIG. 3F, FIG. 3G, FIG. 3H, FIG. 3I, FIG. 3J, FIG. 3K and FIG. 3L; as well as the 20 kD, 52 kD, and 67 kD species human TR2 polypeptides having the deduced amino acid sequences of 184, 483, 467, and 603 residues set out in FIG. 4A, FIG. 4B, FIG. 4C, FIG. 4D, FIG. 5A, FIG. 5B, FIG. 5C, FIG. 5D, FIG. 6A, FIG. 6B and FIG. 6C, respectively. The preferred 79 kD and 98 kD hAR and rAR polypeptides may be produced in vitro and are characterized by a capacity to specifically bind androgens with high specificity and by their immunoprecipitatability by human auto-immune anti-androgen receptor antibodies. The preferred 20 kD, 52 kD, and 67 kD TR2 polypeptides may be produced in vitro and are characterized by their ability to interact with TR-2 antibodies and to interact with DNA.

Other aspects and advantages of the present invention will be apparent upon consideration of the following detailed description thereof which includes numerous illustrative examples of the practice of the invention, reference being made to the drawing wherein:

BRIEF DESCRIPTION OF FIGURES

Figure 3H:
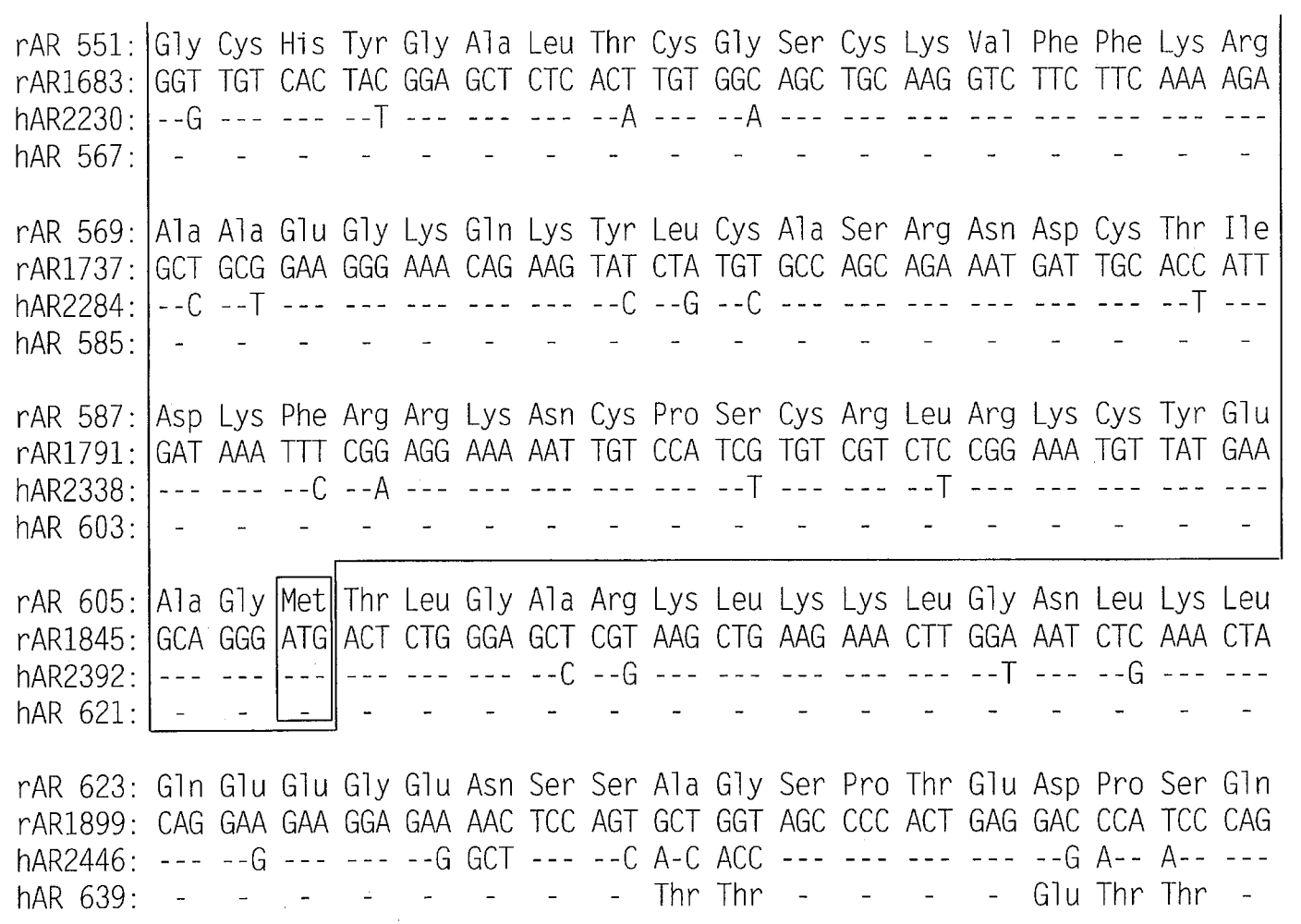

FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L provides a 3715 base pair nucleotide sequence for a human androgen receptor (hAR) DNA clone and the deduced sequence of 734 and 918 amino acid residues for hAR proteins; and in addition provides a 3218 base pair nucleotide sequence for a rat androgen receptor (rAR) DNA clone and the deduced sequences of 733 and 902 amino acids for two rAR species;

FIG. 4A, FIG. 4B, FIG. 4C, and FIG. 4D provides a 2029 base pair nucleotide sequence for a human TR2 DNA clone and a deduced sequence of 483 amino acids for a "TR2-5" species with a calculated molecular weight of 52,982 daltons and a deduced sequence of 184 amino acids for a "TR2-7" species with a calculated molecular weight of 20,528 daltons.

FIG. 5A, FIG. 5B, FIG. 5C, and FIG. 5D provides a 1785 base pair nucleotide sequence for a human TR2 DNA clone and a deduced sequence of 467 amino acids for a "TR2-9" species with a calculated molecular weight of 50,849 daltons; the amino acid sequence in the DNA-binding domain is boxed. The polyadenylation signal AATAAA is underlined.

FIG. 6A, FIG. 6B, and FIG. 6C provides a 2221 base pair nucleotide sequence for a human TR2 DNA clone and a deduced sequence of 603 amino acids for a "TR2-11" species with a calculated molecular weight of 67,223; the amino acid sequence in the DNA-binding domain is boxed. The polyadenylation signal AATAAA is underlined.

FIG. 7A, FIG. 7B, and FIG. 7C provides an amino acid sequence alignment of the cysteine-rich DNA binding domain of human androgen receptor, glucocorticoid receptor, mineralocorticoid receptor, progesterone receptor, estrogen receptor, TR2, rat AR, chick vitamin D receptor (c-VDR), and the v-erb A oncogene product of avian erythroblastosis virus.

FIG. 9A, FIG. 9B, FIG. 9C, FIG. 9D, FIG. 9E, FIG. 10A, FIG. 10B, FIG. 10C, FIG. 10D, FIG. 10E, FIG. 11A, FIG. 11B, FIG. 11C and FIG. 11D illustrate, respectively, the in-frame fusion of three different parts of the AR gene (the N-terminal, the DNA-binding domain and the androgen-binding domain) to the N-terminal half of the trpE gene using pATH expression vectors.

DETAILED DESCRIPTION

Figure 1:
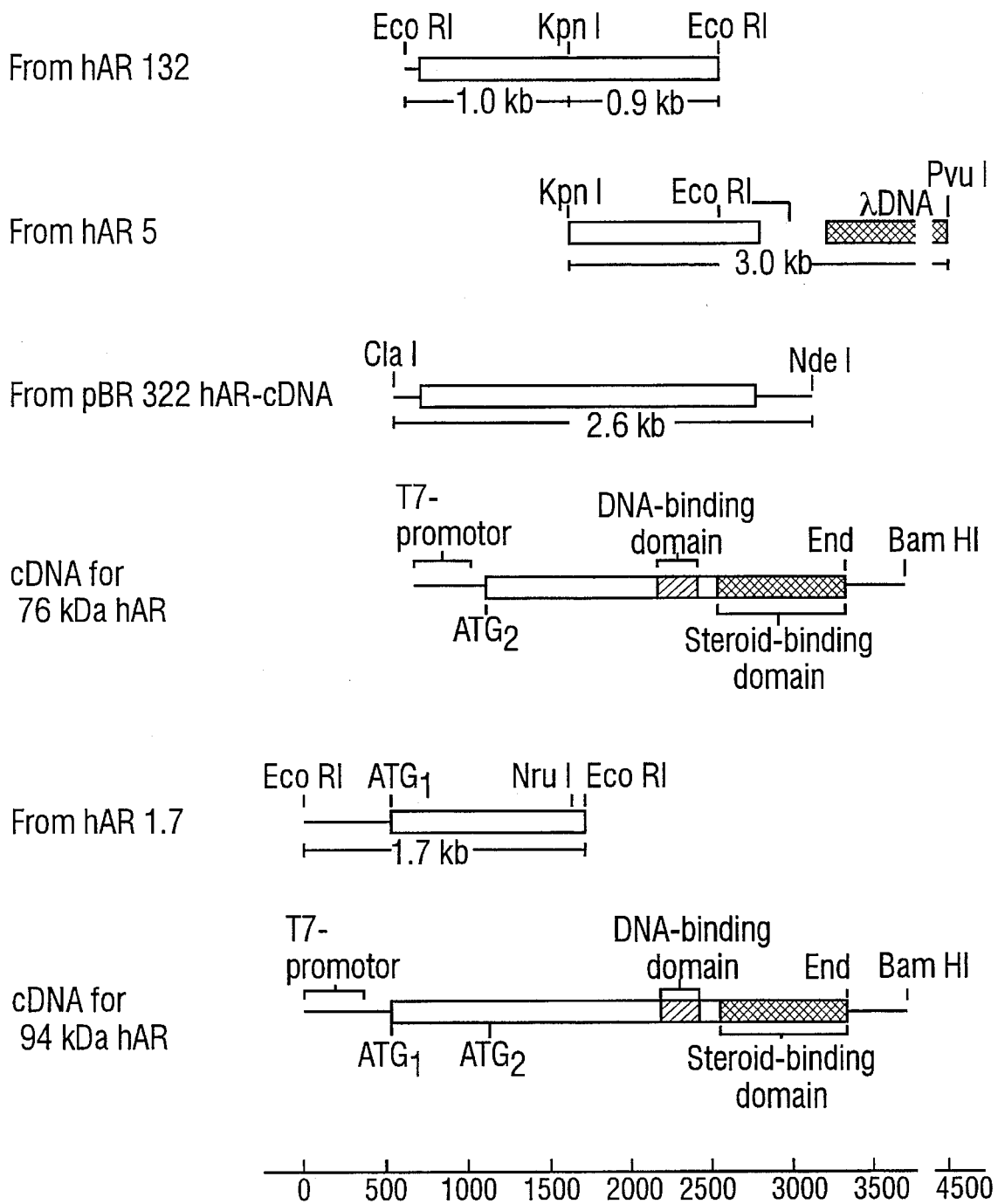
FIG. 1 illustrates the strategy employed in construction of a human androgen receptor cDNA vector.

The following examples illustrate practice of the invention. Example 1 relates to the isolation, preparation, and partial structural analysis of cDNA for human and rat androgen receptors. Example 2 relates to confirmation of the presence on the human X-chromosome of an AR-type cDNA sequence. Example 3 relates to the preparation of human and rat cDNAs containing AR-type cDNA from different clones and ligation into the pGEM-3Z plasmid. Example 4 relates to transcription and translation of the AR-type cDNA plasmid DNA. Example 5 relates to steroid binding activity of the expression product of Example 4. Example 6 relates to the binding activity of the expression product of Example 4 to human auto-antibodies. Example 7 relates to the characterization of TR2-cDNA. Example 8 relates to the in vitro transcription and translation of TR2-cDNA. Example 9 relates to the binding activity of TR2-cDNA expression product. Example 10 provides a schematic comparison of the four variants of human TR2 receptors. Example 11 relate to the androgen regulation of TR2 mRNA levels in the rat ventral prostate. Example 12 relates to recombinant expression systems of the invention. Example 13 relates to the production of fusion proteins and their use in producing polyclonal and monoclonal antibodies according to the invention. Example 14 relates to use of DNA probes of the inventions. Example 15 relates to development of transgenic animals by means of DNA sequences of the invention.

These examples are for illustrative purposes only and are not intended in any way to limit the scope of the invention.

EXAMPLE 1

Preparation and Partial Structural Analysis of cDNA for Human and Rat Androgen Receptors The isolation of cDNA for human androgen receptor (hAR) and rat androgen receptor (rAR) was accomplished using λGT11 cDNA libraries. The human testis and prostate λGT11 libraries were obtained from Clontech Co., Palo Alto, Calif. and a rat ventral prostate λGT11 library in *E. coli* Y1090 was constructed as described in Chang, et al., *J. Biol. Chem.*, 262:11901 (1987). In general, clones were differentiated using oligonucleotide probes specific for various steroid receptors. The cDNA libraries were initially screened with a set of 41-bp oligonucleotide probes designed for homology to nucleotide sequences in the DNA-binding domain of glucocorticoid receptors (GR), estrogen receptors (ER), progesterone receptors (PR), mineralocorticoid receptors (MR), and the v-erb A oncogene product of avian erythroblastosis virus. The set of probes had the following sequence: TGTGGAAGCTGT/CAAAGTC/AT-TCTTTAAAAGG/AGCAA/GTGGAAGG.

The plaques were replicated on a nitrocellulose filter and screened with 5'-end $^{32}$P-labeled 41-bp oligonucleotide probes. The conditions of hybridization were 25% formamide, 5 X Denhardt's solution (0.1% Ficoll 400, 0.1% polyvinylpyrrolidone, 0.1% bovine serum albumin), 0.1% SDS, 5 X SSC (1 X SSC is 150 mM NaCl, 15 mM sodium citrate), 100 μg/ml denatured salmon sperm DNA, and 1 μg/ml poly(A) at 30° C. Filters were washed with a solution containing 0.1% SDS, 0.05% sodium pyrophosphate and 0.4 X SSC at 37° C.

A less stringent hybridization condition (2 X SSC at 37° C.) was used for the first screen employing the 41 bp probes. The remaining clones were then probed again at more stringent conditions by reducing the concentration of SSC, eventually to 0.4 X SSC at 37° C. or by increasing the temperature, or by increasing the concentration of formamide. In some procedures, 5 X SSC, 8% dextran sulfate, and 20% formamide, at 42° C. was employed and the result was equivalent to that obtained with 0.6 X SSC.

From approximately 3×10$^6$ human testis recombinants and 6×10$^5$ rat ventral prostate recombinants, 302 and 21 positive clones, respectively, were obtained.

Based on the assumption that AR might have a cysteine-rich DNA binding domain highly homologous to the DNA-binding regions of other steroid receptors, positive clones from the first screenings were probed with 5'-end $^{32}$P-labeled 24-bp oligonucleotides specific for the various steroid receptors for the possible presence of cDNA for AR through a process of elimination. The GR-cDNA clones were eliminated by screening with two GR-specific 24-bp probes that had nucleotide sequences identical to nucleotide segments immediately next to the 5'-end or the 3'-end of the DNA binding-region of hGR-cDNA, i.e., TGTAAGCTCTCCTCCATCCAGCTC and CAGCAGGC-CACTACAGGAGTCTCA. 244 and 14 clones, respectively, were eliminated as hGR- and rGR-cDNA clones.

Using similar procedures involving four 24-bp probes for the 5'-end of PR(CCGGATTCAGAAA/GCCAGT/CCA-GAGC) and two 24-bp probes for the 3'-end of ER(GCA/CGACCAGATGGTCAGTGCCTTG), no ER- or PR-cDNA clones were detected in the human testis library. In the rat prostate library, no ER-cDNA clones were detected but one positive clone was obtained with hPR-specific 24 bp probes.

Following this process of eliminating clones putatively encoding other steroid receptors, the DNA inserts in the remaining clones were analyzed by restriction mapping and subcloned into M13 vectors for di-deoxy sequence analysis. See, Chang, et al., *J. Biol. Chem.*, 262:2826 (1987). Nucleotide sequence analysis allowed four clones to be identified as hMR-cDNA clones.

Through this stepwise process of elimination, 54 human testis clones and 6 rat prostate clones were selected and were then categorized into two groups. The first group, designated "TR2-type" cDNA comprised 30 human testis clones having sequences that overlap to form a 2.1 kb cDNA. The second group, designated "AR-type" cDNA comprised 24 human testis and 6 rat prostate clones having sequences that overlap to form a cDNA of about 2.7 kb.

EXAMPLE 2

Confirmation of the Presence on the Human X-Chromosome of an AR-type cDNA Sequence Rather than a TR2-type cDNA Sequence The length between the putative polyadenylation signal (AATAAA) and the 5'-end in the "TR-2 type" cDNA is only 2.0 kb, which is considerably shorter than that for the cDNA of other steroid receptors. Therefore, it was suspected that the "AR-type" cDNA, rather than the "TR2-type" cDNA, encoded androgen receptor. To obtain additional information, a human X-chromosome library prepared according to Kunkel, et al., *Nucleic Acids Research*, 11:7961 (1983) was probed with the TR2-type cDNA and AR-type cDNA of Example 1. With TR2-type cDNA fragments, no positive clones were detected, while 3 positive clones were obtained with a 1.9 kb fragment of AR-type cDNA from a human testis (clone AR 132), thereby confirming the presence of an AR-type cDNA sequence on the human X-chromosome. Because the X-chromosome has been implicated as the chromosome which contains an AR gene [Lyon, et al., *Nature (London).*, 227:1217 (1970); Meyer, et al., *Proc. Nat'l. Acad. Sci. (USA)*, 72:1469 (1975); and Amrhein, et al., *Proc. Nat'l. Acad. Sci. (USA)*, 73:891 (1976)], this information suggested that "AR-type" cDNA, but probably not the "TR2-type" cDNA, contained the DNA sequence that could encode for androgen receptor.

Two human clones containing DNA inserts that overlapped to form a 2.7 kb cDNA were designated AR 132 and AR 5. Two rat clones containing DNA inserts that overlapped to form a 2.8 kb cDNA were designated rAR 1 and rAR 4. After restriction enzyme digestion, the DNA segments from these AR-type clones were ligated, selected and amplified using pBR322 and. pGEM-3Z vectors as described in Example 3 below.

EXAMPLE 3

A. Preparation of a Human cDNA Containing AR-type cDNA from Two Different Clones and Ligation Into the Cloning Vector pGEM-3Z Plasmid FIG. 1 relates to the strategy employed in the construction of a full length hAR-cDNA clone. cDNA of clone AR 132 was digested with Eco RI to obtain a 1.9 kb fragment which was then digested with Kpn I to provide a 1 kb Eco RI-Kpn I fragment. This 1 kb fragment was ligated to a 3 kb fragment obtained by digestion of clone AR 5 with Kpn I and Pvu I. The resulting 4 kb fragment was inserted into Eco RI and Pvu I-digested pBR322 vector and used to infect *E. coli* DH5α. The transformed clones were selected by tetracycline-resistance. The plasmid with the DNA insert was digested with Cla I and Nde I to obtain a 2.6 kb fragment. The fragment was blunt-ended with the Klenow fragment of *E. coli* DNA polymerase I and ligated to the cloning vector pGEM-3Z plasmid DNA (Promega Biotec, Madison Wis.) which was previously blunt-ended by digestion with Sma I. *E. coli* DH5 α cells were transformed with the plasmid so formed (designated plasmid PhAR3600) and colonies containing the plasmid were selected by ampicillin resistance and amplified. *E. coli* DH5α cells, transformed with plasmid PhAR3600, were designated EC-hAR3600 and were deposited with the American Type Culture Collection, 12301 Parklawn Drive, Rockville, Md. 20852 on Jan. 25, 1989 under Accession No. 67879.

The plasmid DNA was isolated and its structure analyzed by restriction enzyme mapping and sequencing. The 2.0 kb hAR fragment obtained by NruI-BamHI digestion of a 2.6 kb hAR in pGEM3Z was then ligated to another 1.6 kb ECORI-NruI fragment of hHR to obtain the full length 3715 bp hAR. The open reading frame is about 2.8 kb which is sufficient to code for a protein with more than 900 amino acids. Near the middle of the protein is a cysteine-rich region with a 72 amino acid sequence highly homologous to regions in other steroid receptors considered to be the DNA binding domain.

Figure 2:
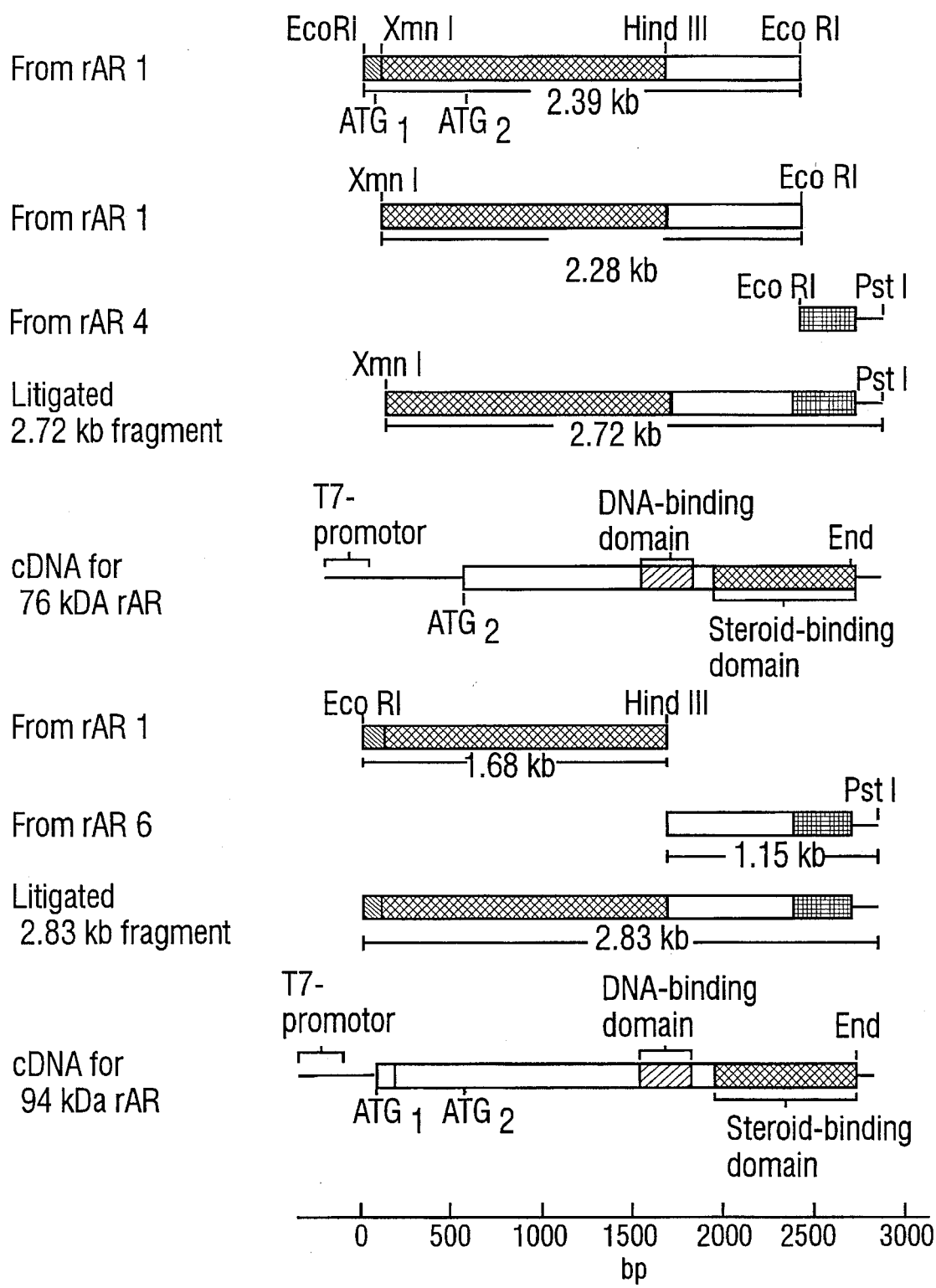
FIG. 2 illustrates the strategy employed in construction of rat androgen receptor cDNA vectors.

As set out in detail below and illustrated in FIG. 2, formation of "full length" rat AR clones by slightly varying procedures results in constructions providing RNA transcripts translatable to 79 kD and 98 kD protein products.

B. Preparation of a Rat 2.7 kb cDNA and Ligation Into the Cloning Vector pGEM-3Z Plasmid The 2.4 kb Eco RI-Eco RI cDNA insert of clone rAR 1 was digested with Xmn I to obtain a 2.3 k b fragment. This 2.3 kb Xmn I-EcoR I fragment was ligated to a 400 bp fragment that was obtained by digestion of another cDNA clone insert (Eco RI-Eco RI insert of rAR 4) with Pst I. The ligated 2.7 kb fragment was inserted into Sma I and Pst I-digested pGEM-3Z vector and used to infect *E. coli* DH5α. The *E. coli* DH5α cells were transformed with the plasmid and colonies containing the plasmid were selected by ampicillin resistance and amplified. These cells were designated EC-rAR 2830 and were deposited with the American Type Culture Collection, 12301 Parklawn Drive, Rockville, Md. 20852 on Jan. 25, 1989 under Accession No. 67878. As noted in FIG. 2, this construction allowed for a transcription product translated beginning with the second of two in-frame methionine-specifying codons (designated $ATG_2$).

C. Preparation of a Rat 2.83 kb cDNA Ligation Into the Cloning Vector pGEM-3Z Plasmid The 2.4 kb Eco RI-Eco RI cDNA insert of rAR 1 was digested with Hind III to obtain a 1.68 kb fragment. The 1.68 kb Eco RI-Hind III fragment was ligated to a 1.15 kb DNA fragment obtained by digestion of another cDNA clone insert (rAR 6) with Hind III and Pst I. The ligated 2.83 kb fragment was inserted into Eco RI and Pst I-digested pGEM 3Z vector and used to infect *E. coli* DH5α. *E. coli* (DH5α) cells were transformed with the plasmid and colonies containing the plasmid were selected by ampicillin resistance and amplified. As noted in FIG. 2, this construction allowed for a transcription product translated beginning at the first of two in-frame methionine-specifying codons (designated $ATG_1$).

FIG. 3A, FIG. 3B, FIG. 3C, FIG. 3D, FIG. 3E, FIG. 3F, FIG. 3G, FIG. 3H, FIG. 3I, FIG. 3J, FIG. 3K, and FIG. 3L provides the nucleotide sequence of the DNA sequence of the longer "full length" rat and human AR clones and includes the deduced amino acid sequences. The first and second methionine-specifying codons are designated at amino acid positions 1 and 170 of rAR and positions 1 and 185 of hAR.

EXAMPLE 4

Transcription and Translation of the Human AR-type cDNA Plasmid in a Rabbit Reticulocyte Lysate System pGEM-3Z vector (20 µg) containing 2.6 kb hAR DNA segment, as described in Example 3, was linearized with restriction enzyme Bam HI, phenol/chloroform extracted, and precipitated with ethanol. The linearized plasmid was transcribed in a reaction mixture containing 40 mM Tris-HCl, pH 7.5, 6 mM $MgCl_2$, 2 mM spermidine, 10 mM NaCl, 10 mM DTT, 500 µM each of ATP, GTP, CTP, and UTP, 160 units ribonuclease inhibitor, 5 µg plasmid, 30 units T7 RNA polymerase (Promega Biotec, Madison, Wis.) and diethylpyrocarbonate (DEPC)-treated water to a final volume of 100 µl. T7 RNA polymerase was used in the transcription of the plasmid DNA, because a T7 promotor, rather than the SP6 promotor, was found ahead of the 5'-end of the ligated AR-cDNA.

The reaction was allowed to proceed for 2 hrs. at 40° C. RQ1 DNase I (5 units) was added and the reaction continued for 15 mins. at 40° C. The reaction mixture was extracted with phenol/chloroform (1:1) and then with chloroform. RNA product was precipitated by the addition of 0.1 volume of 3M Na-acetate and 2.5 volumes of ethanol, re-suspended in 0.5M NaCl, and re-precipitated with 2.5 volumes of ethanol. RNA transcribed was isolated and then translated in a rabbit reticulocyte lysate system.

Translation of RNA was carried out in a micro-coccal nuclease-treated rabbit reticulocyte lysate (Promega Biotec, Madison, Wis.) pre-mixed kit (100 µl) in the presence of 8 µg mRNA, 40 µCi of [$^{35}$S] methionine (800 Ci/mmol; Amersham Co., Arlington Heights, Ill.) and 100 µM each of amino acid mixture without methionine. The reaction was allowed to proceed for 1 hour at 30° C. To quantitate the incorporation of radioactive methionine, 3 µl of the reaction mixture were added to 1 ml of 1M NaOH containing 1.5% $H_2O_2$, 1 mM methionine, and 0.04% bovine serum albumin. The mixture was incubated for 15 mins. at 37° C. to hydrolyze [$^{35}$S] methionine charged tRNA. The radioactive protein products were precipitated by the addition of 1 ml of 25% tricholoacetic acid and the radioactivity associated with the precipitates was determined.

By SDS-PAGE (8% acrylamide gel) analysis, performed as described in Saltzman, et al., *J. Biol. Chem.*, 262:432 (1987), it was found that a 79 kD protein comprised more than 85% of the translated products.

EXAMPLE 5

Binding Activity of the 79 kD hAR Protein to a Synthetic Androgen

To study the steroid binding activity of the protein coded for by the cloned cDNA, the reticulocyte lysate of Example 4, containing the newly synthesized protein was incubated with 17α[$^3$H]-methyl-17β-hydroxy-estra-4,9,11-trien-3-one ([$^3$H] R1881), a potent synthetic androgen that binds AR with high affinity [Liao, et al., *J. Biol. Chem.*, 248:6154 (1973)].

Specifically, RNA transcribed from the cloned cDNA, as described in Example 4, was translated in a rabbit reticulocyte lysate system and aliquots of the lysate were then incubated with 5 nM [$^3$H] R1881 (87 Ci/mmol) in the absence or presence of 25 nM, 50 nM, or 250 nM of non-radioactive steroid. The final incubation volume was 100 μl. The radioactive androgen binding was measured by the hydroxylapatite-filter method as described in Liao, S., et al., *J. Steroid Biochem.*, 20:11 (1984). The result was expressed as a percentage of the radioactivity bound in the control tube (5000 dpm) without additional non-radioactive steroid and is listed in Table 1.

TABLE 1

| | Androgen-specific binding of hAR coded by cloned cDNA | | |
|---|---|---|---|
| Non-radioactive | [$^3$H] R1881-bound (% of control) | | |
| steroid added | 25 nM | 50 nM | 250 nM |
| R1881 | 13 | 10 | 1 |
| 5α-dihydrotestosterone | 25 | 17 | 6 |
| 5β-dihydrotestosterone | 89 | 89 | 81 |
| 17β-Estradiol | 91 | 91 | 86 |
| Progesterone | 100 | 91 | 92 |
| Dexamethasone | 100 | 93 | 93 |
| Hydrocortisone | 96 | 90 | 90 |
| Testosterone | 38 | 28 | Not tested |

As shown in Table 1, the active natural androgen, 17β-hydroxy-5α-androstan-3-one(5α-dihydro-testosterone) competed well with [$^3$H] R1881 binding, but the inactive 5β-isomer did not compete well with [$^3$H] R1881 suggesting that it does not bind tightly to AR. The binding activity was steroid specific; dexamethasone, hydrocortisone, progesterone, and 17β-estradiol did not compete well with the radioactive androgen for binding to the 79 kD protein.

Similar steroid binding specificities have also been observed for rAR coded for by cloned cDNA. Chang, C., et al., *Proc. Nat'l. Acad. Sci. (USA).*, 85:7211–7215 (1988).

Using the hydroxylapatite filter assay method, it was observed that approximately one molecule of the $^{35}$S-labelled 79 kD protein obtained from the lysate bound about one molecule of the tritiated androgen at a saturating concentration of ligand. By Scatchard plot analysis, the apparent dissociation constant was 0.31 nM, which is similar to the binding constant (0.65 nM) reported previously for AR of rat ventral prostate as reported in Schilling, et al., *The Prostate*, 5:581 (1984).

EXAMPLE 6

Binding Activity of the 79 kD Protein to Human Auto-antibodies

It has previously been reported [Liao, et al., *Proc. Nat'l. Acad. Sci. (USA)*, 82:8345 (1985)] that some older men with prostate cancers have high titers of auto-immune antibodies to AR in their serum samples. The ability of human auto-antibodies to recognize the 79 kD protein made by the reticulocyte lysate system was therefore studied. The receptor protein made in the lysate system of Example 4 was incubated with [$^3$H] R1881 to allow the formation of radioactive androgen-androgen receptor (A-AR) complexes and was then mixed with serum containing auto-antibodies.

Reticulocyte lysate containing translated AR was incubated with [$^3$H] R1881, as described in Example 4, and then incubated again in either the presence of or absence of 5 μl of human male serum containing antibodies to AR (anti-AR serum) for 4 hrs. at 4° C. Rabbit serum containing anti-human immuglobulins (Anti-IgG) was then added as the second antibody. After 18 hrs. of incubation at 4° C, the mixture was centrifuged and the radioactivity associated with the precipitate was estimated. Human female serum, not containing anti-AR antibody, was also used for comparison.

The results shown in Table 2 below, indicate a quantitative immunoprecipitation of the radioactive A-AR complexes in the presence of both the high titer human serum and a rabbit anti-human immunoglobulin IgG. By SDS-PAGE, it was also observed that the immunoprecipitated protein was the 79 kD protein.

TABLE 2

| | Anti-human immunoglobulin-dependent precipitation of hAR made by the translation of RNA transcribed from cloned cDNA | |
|---|---|---|
| Sample incubated with [$^3$H]R1881 | Anti-serum addition | Immuno-precipitable radioactivity (dpm) |
| AR coded by cDNA[a] | None | 32 |
| | +Anti-AR serum + Anti-IgG | 8212 |
| | +Female serum + Anti-IgG | 430 |
| | +Anti-IgG | 8 |
| Heated AR[b] | +Anti-AR serum + Anti-IgG | 42 |
| BMW-lysate[c] | +Anti-AR serum + Anti-IgG | 204 |

[a]8500 dpm of the radioactive AR complexes made were used.
[b]Reticulocyte lysate containing AR was heated at 50° C. for 20 mins. to inactivate receptor and release the radioactive androgen bound before the addition of antiserum.
[c]Brome Mosaic Virus RNA was used in the reticulocyte lysate translation system instead of RNA transcribed from cloned cDNA.

EXAMPLE 7

Characterization of "TR2-type" cDNA

Of the more than 40 TR2-type human cDNA clones obtained, including the 30 described in Example 1, the clone designated TR2-5 was found to be 2029 base pairs in length as indicated in FIG. 4A, FIG. 4B, FIG. 4C, and FIG. 4D. The open reading frame between the first ATG and terminator TAA can encode 483 amino acids with a calculated molecular weight of 52 kD. The putative DNA binding region is underscored. The putative initiator ATG matched closely with Kozak's concensus sequence for active start codons. [See, Kozak, M., *Nature*, 308:241 (1984).] Two triplets upstream of this ATG codon is an in-frame terminator (TAA) further supporting initiator function for the ATG.

Eleven of the 30 TR2-type clones of Example 1, as represented by the clone designated TR2-7, contain an internal 429 bp insertion between nucleotide sequence 669 and 670 (designated by an asterisk in FIG. 4A, FIG. 4B, FIG. 4C, and FIG. 4D. This internal insertion introduces a termination codon TAG (underscored in the insert sequence footnote) which reduces the open reading frame to 184 amino acids with a calculated molecular weight of 20 kD. It is likely that the insertion in these 11 TR2 clones (or deletion in the 19 other TR2 clones) represents either the existence of two types of mRNA in the human testis or an artifact of cDNA construction. In the 3'-nontranslated region, a eukarotic polyadenylation signal AATAAA is present between the nucleotide sequence 2000 and 2007 of the TR2-5 clone.

TR2-9 receptor cDNA was isolated from a human prostate cDNA library has 1785 bp FIG. 5A, FIG. 5B, FIG. 5C, and FIG. 5D. The open reading frame from the first ATG to TAA encoded 467 amino acids with a calculated molecular weight of 50,849 daltons.

TR2-11 receptor cDNA has 2221 bp, with a shorter 5'-untranslated region FIG. 6A, FIG. 6B, and FIG. 6C. The open reading frame encoded a polypeptide of 603 amino acids with a calculated molecular weight of 67,223 daltons. The predicted initiator ATG of these two cDNA sequences matches well with Kozak's consensus sequence for an active start codon (Kozak, M., *Nature*, 308:241–246 (1984)) and there is an in-frame stop codon TAG upstream of the initiation ATG in each cDNA sequence. In the 3'-un-translated region, a eukaryotic polyadenylation signal AATAAA is present between nucleotide numbers 1710–1715 for the TR2-9 receptor and between 2180–2185 bp for the TR2-11 receptor.

Other variants of TR-2 with open reading frames at the putative ligand-binding domains may code for receptors for new hormones or cellular effectors. It is anticipated that the knowledge of TR2-cDNA sequences will be utilized in isolation and structural analysis of other cellular receptors, their genes, and ligands (endogenous or therapeutic agents) that can regulate cellular growth and functions in both normal and diseased organs.

There is a conservation of the DNA-binding domain for TR2 receptors and for other members of the steroid hormone receptor family. The putative DNA-binding domain of TR2 receptor shares 50–60% homology with that of other steroid receptors and TR3 receptor (Chang, C., Kokontis, J., and Liao, S., *Science*, 240:324–326 (1988); Chang, C., Kokontis, J., Chang, C. T., and Liao, S., *Nucleic Acid Res.*, 22:9603 (1987); Green, S., Walter, P., Kumar, V., Krust, A., Bornert, J. M., Argos, P., and Chambon, P., *Nature*, 320:134–139 (1986); Arriza, J. L., Weinberger, C., Cerelli, G., Glaser, T. M., Handelin, B. L., Housman, D. E., and Evans, R. M., *Science*, 237:268–275 (1987)). TR3 receptor is another member of the steroid receptor family, which may be a human homologue of the mouse NUR/77 gene product (Chang, C., Lau, L., Liao, S., and Kokontis, J., in the Steroid/Thyroid Hormone Receptor Family and Gene Regulation, Birkhauser Verlag, Basel, Boston, Berlin, pp. 183–193 (1988); Hazel, T. G., Nathans, D., and Lau, L. F., *Proc. Nat'l. Acad. Sci. USA*, 85:8444–8448 (1988)). The 26 amino acids in the DNA-binding domain of TR2 receptor are identical to those in the DNA-binding domain of all other known steroid receptors. The positions of conserved amino acid residues have been proposed to be involved in the formation of DNA-binding domain "Zinc fingers" (Weinberger, C., Hollenberg, S. M., Rossenfeld, M. G., and Evans, R. M., *Nature*, 318:670–672 (1985)).

Figure 7A:
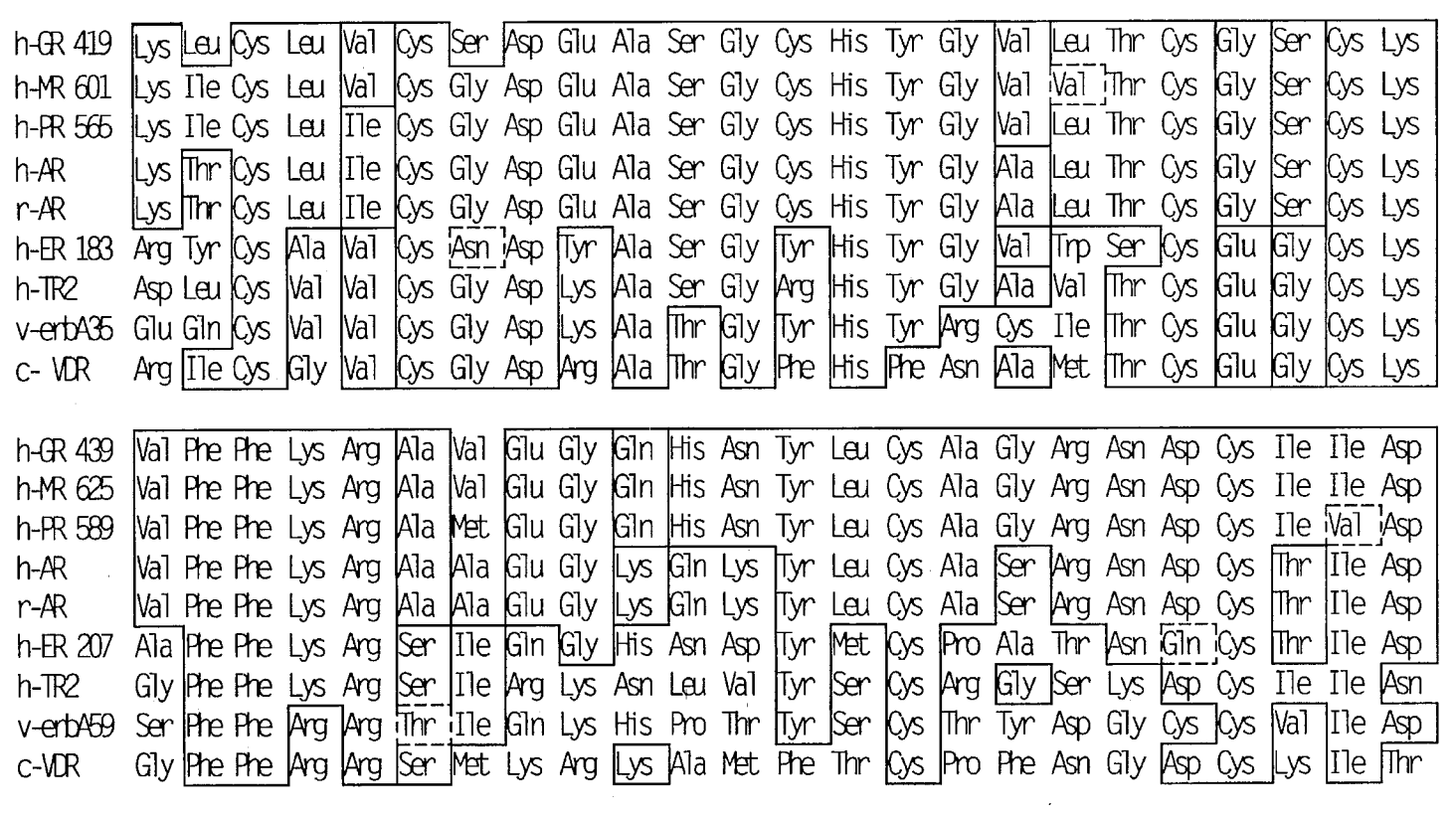

FIG. 7A and FIG. 7B depicts an amino acid sequence alignment of the cysteine-rich DNA binding domain of human androgen receptor, glucocorticoid receptor, mineralocorticoid receptor, progesterone receptor, estrogen receptor, human TR2 protein, rat AR, chick vitamin D receptor (c-VDR), and the v-erb A oncogene product of avian erythroblastosis virus. The numbers in the left margin represent the positions of amino acid residues in the individual receptors. Common residues are boxed with solid lines. The residues in dotted boxed represent those not in common with those in the solid boxes. V-erb A has two more amino acids at the starred position.

In this region, the human and rat cDNAs for AR have identical amino acid sequences, although for some amino acids different codons are employed. Also in this region, the homology between human AR or rat AR and other receptors is as follows: glucocorticoid receptor (GR), 76.4%; mineralo-corticoid receptors (MR), 76.4%; progesterone receptors (PR), 79.2%; estrogen receptors (ER), 55.6%; TR2, 45.8%; chick vitamin D receptor (cVDR), 40.3%; and the v-erb A oncogene product of avian erythroblastosis virus, 40.3%. In the putative region for steroid binding, which has about 200 amino acids near the —COOH terminal of steroid receptors, the homology between human AR or rat AR and hGR, hMR, or hPR is about 45–55%, whereas the homology between human AR and rat AR and hER is less than 20%. Thus, human and rat AR appear to be more closely related to GR, MR, and PR, than to v-erb A or to receptors for estrogen, vitamin D, and thyroid hormones.

The DNA binding domain of TR2 (amino acids 111 to 183) has a high homology with the steroid receptor superfamily as follows: retinoic acid receptor (RAR), [Giguere, et al., *Nature*, 330:624 (1987)], 65%; thyroid receptor ($T_3R$) [Sap, et al., *Nature*, 324:635 (1987)], 59%; mineralocorticoid receptor (MR), [Arriza, et al., *Science*, 235:268 (1987)], 54%; vitamin $D_3$ receptor ($VD_3R$) [McDonnell, et al., *Science*, 235:1214 (1987)], 53%; hERR1 and hEER2, [Giguere, V., et al., *Nature*, 331:91 (1988)], 51% estrogen receptor (ER), [Hollenberg, et al., *Nature*, 318:635 (1985)], 51%; glucocorticoid receptor (GR) [Hollenberg, et al., *Nature*, 318:635 (1985)], 50%; androgen receptor (AR), 50%; progesterone receptor (PR), 49%; [Loosfelt, et al., *Proc. Nat'l. Acad. Sci., (USA)*, 83:9045 (1986)]. As noted in FIG. 7, the positions of 20 amino acids (9 Cys, 3 Arg, 2 Gly, 2 Phe, 1 Lys, 1 Met, 1 Asp, 1 His) in the putative DNA binding domain are identical among all isolated thyroid steroid receptor genes. It has been proposed that this highly conserved region may be involved in the formation of a DNA binding finger. See, Weinberger, et al., *Nature*, 318:670 (1985). Like the other steroid receptors, TR2 does not have the two extra amino acids (Lys-Asn) found only in the thyroid receptors' DNA binding domain. See, Sap, et al., *Nature*, 324:635 (1987).

EXAMPLE 8

In Vitro Transcription and Translation of TR2 cDNA

The Eco RI-Eco RI DNA inserts from clones TR2-5 and TR2-7 were isolated and ligated to an EcoR1 digested pGEM-3Z vector for in vitro transcription essentialy as described in Example 3. *E. coli* DH5α cells, transformed with these plasmids were designated EC TR2-5 and EC TR2-7 and were deposited Jan. 25, 1989 with the American Type Culture Collection, 12301 Parklawn Drive, Rockville, Md. 20852 under Accession Nos. 67877 and 67876.

Transcribed RNA was then translated in a rabbit reticulocyte lysate system. By SDS-polyacrylamide gel electrophoresis (PAGE), it was found that the major translated product of TR2-7, which has an internal 429 bp, insertion, was a 20 kD protein. The major translated product of TR2-5 was a 52 kD protein.

TR2-11 receptor cDNA was isolated and ligated to EcoRI-digested pGEM-3Z vector for in vitro transcription, essentially as described in Example 3. *E. coli* DH5α cells, transformed with this plasmid, were designated EC TR2-11 and deposited on Nov. 14, 1989; with the A.T.C.C. under accession No. 68173. Transcribed RNA was translated in a rabbit reticulocyte lysate system. SDS polyacrylamide gel analysis showed a major band around 67 kd, consistent with the calculated molecular weight of 67,223 daltons.

To further characterize these translated proteins, the translation lysate was passed over a DNA cellulose column. The bound product was then eluted, concentrated and applied to SDS-PAGE. The results indicated that the translated proteins were indeed DNA-binding proteins.

EXAMPLE 9

Binding Activity of TR2-5, TR2-7 and TR2-11 cDNA Expression Product

To study the steroid binding activity of the translation products of the TR2-5, TR2-7, and TR2-11 clones, the products were incubated with all major classes of steroids, including androgens, progesterone, glucocorticoid and estrogen but no significant binding with the above steroids was observed. This does not necessarily rule out asteroid binding function for these proteins. Possibly the TR2-5, TR2-7, and TR2-11 expression products' steroid binding activity may involve some post-translation modifications missing in the rabbit reticulocyte lysate system. Alternatively, the TR2-5, TR2-7, and TR2-11 translated proteins may be steroidal independent or may bind to an unidentified ligand present in the human testis or rat ventral prostate, or, alternatively, may be dependent upon an unknown steroidal or non-steroidal hormone.

The size of TR2 mRNA was determined by Northern blot analysis with TR2-5 cDNA insert as a probe. One 2.5 kb band was detected which should include enough sequence information to code for a 52 kD protein. The TR2 mRNA tissue distribution was also analyzed by dot hybridization. The hybridization was visualized by densitometric scanning of the autoradiographs, individual dots were cut and radioactivity measured by liquid scintillation counting. Chang, et al., *J. Biol. Chem.*, 262:2826 (1987). The results showed that TR2 mRNA was most abundant in the rat ventral prostate with the relative amounts in other tissues being: prostate 100%, seminal vesicle 92%; testis, 42%; submaxillary gland, 18%; liver, 13%; kidney, <1%; and uterus, <1%.

EXAMPLE 10

Schematic Comparison of the Four Variants of Human TR2 receptors

Figure 8:
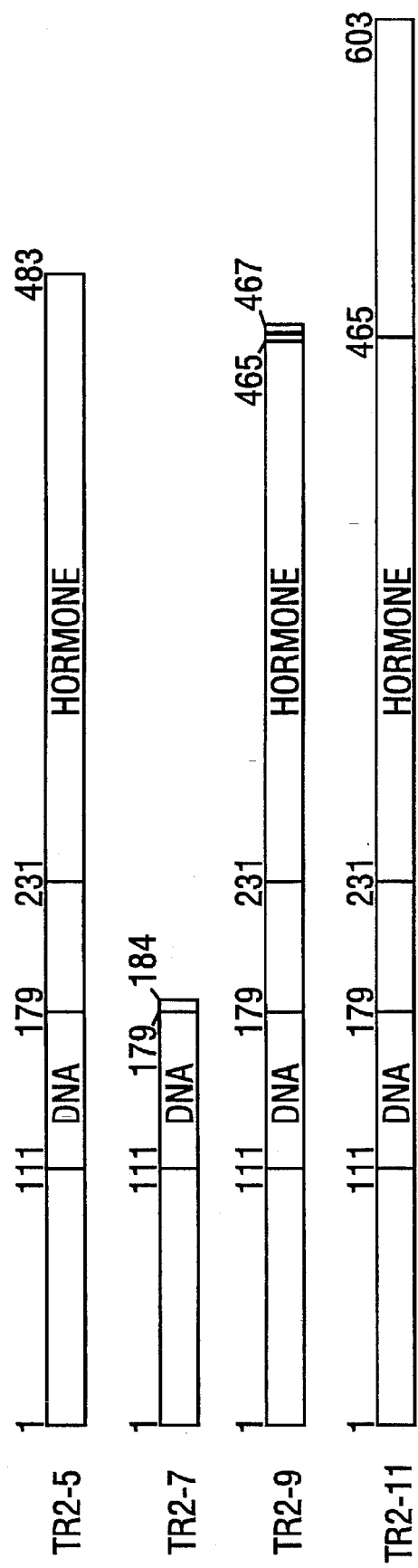
FIG. 8 provides a schematic comparison of the four variants of human TR2 receptors: TR2-5; TR2-7; TR2-9; and TR2-11; numbers above the boxes indicate the positions of amino acid residues. The DNA-binding domain (DNA) and the hormone-binding domain (Hormone) are shown. The sequences for TR2-5, TR2-9, and TR2-11 are identical from amino acid number 1 to 464.
Figure 11C:
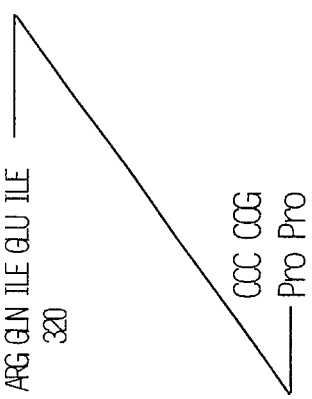

A schematic comparison of four TR2 receptors (TR2-5; TR2-7; TR2-9; and TR2-11) is shown in FIG. 8. TR2-7 receptor contains an internal extra 429 base point segment between nucleotide number 670 and 671 base point, which generates a termination codon and shortens the open reading frame to 184 amino acids. Chang, C., Kokontis, J., *B.B.R.C.*, 155:971–977 (1988).

The sequences of TR2-5, TR2-9, and TR2-11 receptors are identical from amino acid number 1 to 464. However, the C-terminal hormone-binding domains of these three TR2 receptors are different. Chang, C., Kokontis, J., *B.B.R.C.*, 155:971–977 (1988). TR2-9 receptor has 16 fewer amino acids and 3 different amino acids as compared with TR2-5 receptor, due to a 244 bp insertion between nucleotide number 1518 and 1763 of TR2-5 receptor. Evans, R. M., *Science*, 240:889–894 (1988). TR2-11 receptor has more and quite different amino acids in the hormone-binding domain.

The variant forms of TR2 receptors, like multiple forms of thyroid hormone receptors, (Evans, R. M., *Science*, 240:889–894 (1988)), may be very significant in terms of biological function. However, there are differences with respect to tissue specificity and with respect to the degree of homology in the putative DNA-binding domain. Variant thyroid hormone receptors were found in different tissues, indicating tissue specificity of the receptors. In contrast, although TR2-11 receptor cDNA was isolated from human prostate cDNA library, all other TR2 receptor cDNAs (TR2-5, TR2-7, and TR2-9) were isolated from a human testis cDNA library, indicating co-expression in at least one human tissue. The incomplete homology in the DNA-binding domain of thyroid receptors may contribute to the differential target gene specificity. In contrast, the putative DNA-binding domain of TR2 receptors are identical, suggesting that they may act on the same target gene(s). Variant TR2 receptors may be the products of different genes. Alternatively, RNA splicing can generate messages encoding TR2 receptors with multiple hormone-binding domains. If this is the case, regulation at the RNA splicing level may be important during the transition of hormone-dependent organs/tumors to hormone-independent organs/tumors. Also, if TR2 receptors with different hormone-binding domains are able to bind to different natural ligands, or to the same ligand with a differential affinity, the co-expression of variant receptors may provide competition for ligands among receptors, and the activation level of the target genes could be regulated by adjusting the expression ratio of different variant receptors. This expression ratio could vary with tissue-specificity or developmental stage-specificity. Given that in rat, TR2 receptor mRNA was most abundant in the androgen-sensitive ventral prostate (Chang, C., Kokontis, J., *B.B.R.C.*, 155:971–977 (1988)), it is of interest to examine the expression ratio of variant TR2 receptors in normal, neoplastic, or hyperplastic prostate tissue and study their possible roles in prostate growth and development. It is anticipated that a determination of the genomic structure of TR2 receptor genes and the natural TR2 receptor ligand may lead to elucidation of the mechanism by which variant receptors are generated and elucidation of the cellular function of this new member of the steroid hormone receptor superfamily.

EXAMPLE 11

Analysis of Androgen Regulation of AR and TR2 mRNA Levels in the Rat Ventral Prostate Because rat ventral prostate is an androgen-sensitive organ and contains the greatest amount of AR and TR2 mRNA, the effect of androgen depletion and replacement on the mRNA levels was studied by RNA dot hybridization and Northern blot analysis. Total RNA was extracted from the ventral prostate of normal rats, rats castrated and rats previously castrated and treated with 5α-dihydrotestosterone (17β-hydroxy-5α-androstand-3-one). AR mRNA levels per unit of DNA increased 200 to 300% of the level for normal rats within 2 days after castration. Administration of 5α-dihydrotestosterone (5 mg/rat/day) into castrated rats reduced the AR mRNA level to that of normal rats. TR2 mRNA levels, per unit of DNA, were increased to 170% of the normal rat within 2 days after castration. Injection of 5α-dihydrotestosterone (5 mg/rat/day) into castrated rats reduced the TR2 mRNA to the levels of normal rats. Interestingly, the total prostate RNA levels, at the same period of time, were decreased to 40% of the normal level. The effects of androgen on the levels of prostatic TR2 mRNA were further confirmed by flutamide injection experiments. Flutamide, an anti-androgen which antagonizes the effects of 5α-dihydrotestosterone on the ventral prostate weights in castrated rats [Neri, et al., *Invest. Urol.*, 10:123 (1972)], was injected into normal rats for from 2 to 6 days. TR2 mRNA levels were then measured by dot hybridization as described above. The results show that flutamide injection, like castration, increased TR2 mRNA levels. The change in the AR or TR2 protein levels could be due to a change in mRNA stability and utilization or a change in the regulation of gene transcription. The activation or inactivation by androgen of specific genes to different degrees in the same organ may suggest that androgen is involved in the structuring of the pattern of gene expression in the target cell. Also, if androgen-mediated gene repression mechanisms are related to growth of the prostate, then a further study of the mechanism and structure of genes, repressed AR and TR2 mRNA may provide a better understanding of androgen action in the normal and abnormal prostate and other hormone sensitive organs.

Also, defects in the structures of AR and androgen sensitive genes and/or losses of the control of the production and function of these gene products can be the causes of the abnormal growth of androgen sensitive or insensitive tumors like prostate cancers. These lines of research may, therefore, be helpful in designing new diagnostic methods and treatments for patients.

EXAMPLE 12

Expression of Cloned AR-Genes and Androgen Sensitive Genes in Eukaryotic and Prokaryotic Cells The ability of cloned genes to function when introduced into mammalian, yeast, and bacterial cells has proved to be very valuable in understanding the function and regulatory mechanism of genes. Recombinant techniques can provide, in large quantities, gene expression products (proteins) which are not readily obtainable from natural sources. While bacterial systems are very useful in large scale production of those proteins which do not require substantial post-translational modification for optimal biological activity, eukaryotic systems are particularly advantageous because of their ability to correctly modify the expressed proteins to their functional forms.

Using well known techniques, AR-cDNA and TR2-cDNA may readily be used for large scale production of gene products. For this purpose, the most efficient transcription units can be constructed using viral, as well as non-viral, vectors with regulatory signals that can function in a variety of host cells. SV40, pSV2, adenoviruses, and bovine papilloma virus DNA have been used successfully for introduction of many eukaryotic genes into eukaryotic cells and permit their expression in a controlled genetic environment. These and similar systems are expected to be appropriate for the expression of AR- and TR2-genes. To assist gene transfer, the two most widely used methods, the "calcium phosphate precipitation" and the "DEAE-dextran technique" can be used. Genes can be introduced into cells either transiently, where they continue to express for up to 3 days, or, more permanently to form stably transformed cell-lines. The expressed proteins can be detected by androgen binding or antibody assays.

The expression of cloned AR-genes was achieved as follows in a eukaryotic system. NIH 3T3 cells, contact-inhibited cells established from NIH Swiss mouse embryo, were co-transfected with hAR cDNA inserted into pBPVMTH vectors as described by Gorman, "*DNA Cloning*", 2:143–190 D. M. Glover, ed.; (Oxford, Washington, D.C. 1985). Transfected cells were cloned and grown in multiple-well cell culture plates. About 100 individual cell lines were isolated. Of these, 6 demonstrated [$^3$H] R1881-binding activity at least 4-fold the activity of cells transfected with pSV2 vector alone, i.e., without the hAR cDNA sequence.

To express AR cDNA in prokaryotic systems, hAR and rAR cDNAs were inserted into a number of expression vectors including pUR, λGT11, pKK223-3, pKK233-2, pLEX, pATH1, pATH2, pATH10, and pATH11. Vectors with AR cDNA inserts were used to infect *E. coli* strains (JM109, DH5α, Y1089, JM105, and RR1). According to polyacrylamide gel electrophoresis analysis, the infected bacteria can synthesize AR fragments coded for by the AR cDNA inserts. Some of these AR polypeptides are degraded in culture. Amino terminal, DNA-binding, and androgen binding domains were used, as described in Example 13, to construct fusion proteins representing these domains.

EXAMPLE 13

Production of Polyclonal and Monoclonal Antibodies to AR

The isolation of AR in significant amounts from androgen sensitive organs has been exceedingly difficult. Therefore, the high-level expression of hAR or rAR cDNAs, as shown in Example 12, is expected to be an ideal way for the large scale production of AR. In addition, oligopeptides, with sequences identical to the deduced amino acid sequences of portions of AR molecules, can be chemically synthesized inexpensively in large quantities. Both AR produced by expression vectors in eukaryotic or prokaryotic cells and AR oiigopeptides chemically synthesized were used as antigens for the production of monoclonal antibodies as described in greater detail below.

Generally, several chemically synthesized oligopeptides, representing sequences unique to AR, (i.e., PYGDMRLETARDHVLP; CPYGDMRLETARDHVLP; and SIRRNLVYSCRGSKDCIINK) were bound to BSA or KLH carrier proteins and were used to immunize mice. Spleen cells from these mice were fused to myeloma cells to produce hybrid antibody producing cells. Analysis by ELISA (enzyme-linked immunoassay) of the supernatants of 4 hybrid cultures appeared to indicate the presence of immunoglobulin that interacts with AR of rat ventral prostate. It is anticipated that these cells which produce monoclonal antibodies can be injected intraperitoneally into BALB/c mice previously treated with pristane. Ascites fluids can then be harvested and antibodies precipitated with ammonium sulfate.

Expression of Androgen Receptor Fusion Protein in *E. coli*

Three different parts of the AR gene (encompassing the N-terminal domain, the DNA-binding domain and the androgen-binding domain) were fused, in frame, to the N-terminal half of the trpE gene (trpE promoter-the first 969 bp of trpE coding region-multiple cloning region of pUC12) by using the pATH expression vectors as shown in FIG. 9A, FIG. 9B, FIG. 9C, FIG. 9D, FIG. 9E, FIG. 10A, FIG. 10B, FIG. 10C, FIG. 11A, FIG. 11B, FIG. 11C and FIG. 11D respectively. Dieckmann, et al., *J. Biol. Chem.*, 260:1513 (1985).

These constructions resulted in the fusion of approximately 25 kDa of AR, including a portion of the N-terminal domain; 29 kDa of AR, including a major portion of the DNA-binding domain; and 12 kDa of AR, including a portion of the androgen-binding domain; to the 33 kDa trpE protein. Because the trpE protein is insoluble, partially purified induced fusion proteins were obtained simply by lysing the *E. coli* and precipitating the insoluble fusion proteins. After electrophoresis on SDS-polyacrylamide gels, the induced fusion proteins, i.e., those proteins not present in the control pATH vector (no AR gene insert), were sliced from the gels and then used for immunization.

Fusion proteins, other than the three specifically exemplified, can also be constructed using these means.

Production and Purification of Anti-AR Antibodies

Rabbits, rats, and mice were immunized with either SDS-polyacrylamide gel slices containing denatured fusion proteins or electro-eluted, SDS-free, fusion protein, as well as fusion proteins obtained by other protein purification methods. The presence of antibodies to the fusion proteins in the antisera was assayed by ELISA. Positive serum having a higher titer was further assayed by the double antibody precipitation method using rat ventral prostate cytosol [$^3$H] AR as antigen. The results showed that 1 µl of crude serum precipitated 10 to 20 fmole [$^3$H]AR. Anti-AR crude serum was then affinity-purified by differential suspension of immune serum containing TrpE protein(s) (both those TrpE proteins having and those TrpE proteins not having inserted AR sequences) expressed by pATH vectors. The bound antibodies can be removed from the suspension because TrpE protein is insoluble. Antibodies specific against only the trpE protein were removed; antibodies specific for AR were isolated and again confirmed by both ELISA and double antibody precipitation.

Production of Monoclonal Anti-Androgen Receptor Antibodies

The immunized rats were judged ready to be sacrificed for a fusion when their serum tested positive anti-AR antibodies by ELISA. Spleens were removed and grinded to release the cells into DMEM (Dulbeco's Modified Engle's Medium) medium. Through a series of centrifugations using DMEM+ DMEM with Ficoll Hypaque, the spleen cells were isolated. The SP2/0 myeloma cells were grown, split and diluted in 50 ml of DMEM with 20% FCS, 1% MOPS, and 1 X L-Gln for two days before ready for the fusion. SP2/0 cells ($5 \times 10^6$) and $5 \times 10^7$ spleen cells were used in the fusion. After incubating overnight, the fused cells were collected, suspended in DMEM with 1 X H-T, 1 X Methotrexate, 20% FCS, and 1 X PBS and distributed in 96-well plates. Plates were supplemented after 6 days with DMEM and 20% FCS. Hybridomas were identified and assayed, using the ELISA assay of Engrall, et al., *Bio. Chem. et Biophys. ACTA*, 251:427–439 (1971). In this assay, plates were coated with either the AR fusion proteins or the TrpE protein as antigen and read on an ELISA reader.

Only those hybridomas that caused a positive reaction with the AR fusion protein were "limit diluted" to a concentration of 10 cells/ml and were then distributed among half of a 96-well plate. The remaining cells from the original well were transferred to a 24-well plate. Each of these plates had a thymocyte feeder layer. The tymocyte feeder layer was made up of thymus cells isolated from an un-injected rat, purified through centrifugation, irradiated with 1200 to 1400 RADS, and diluted to $1 \times 10^7$ cells/ml of DMEM with 20% FCS.

Positives from these thymocyte 96-well plates were again tested by ELISA. Only those which again tested positive with the AR fusion protein were grown up for monoclonal antibody purification. Three of the wells produced monoclonal antibody against AR. Both ELISA and double antibody assays were positive. The monoclonal antibodies were designated AN1-6, AN1-7, and AN1-15 and the three cell lines were designated HAN1-6, HAN1-7, and HAN1-15; Accession Nos. 10,000; 9,999; and 10,001; respectively, deposited on January 25, 1989 with the American Type Culture Collection, 12301 Parklawn Drive, Rockville, Md. 20852.

Specificity of Anti-AR Antibodies

Sucrose gradient centrifugation was used to characterize the specificity of the three monoclonal anti-AR antibodies and their ability to react with non-denatured [$^3$H]AR.

Cytosol was prepared from the ventral prostates of castrated rates as follows. Rats were castrated by the scrotal route while under anesthesia. They were killed 18 hrs. laters by cervical dislocation and their ventral prostates were removed, minced with scissors, washed in Buffer A (50 mM sodium phosphate, pH 7.5, 1 mM EDTA, 2 mM DTT, 10 mM sodium molybdate, 10% (v/v) glycerol and 10 mM sodium floride) and homogenized in 2× the tissue volume of Buffer A+0.1 mM bacitracin, 1 mM PMSF, and aprotinin (1TIU/ml). The homogenate was centrifuged at 5,000×g for 10 mins., adjusted to 10 nM $^3$H-androgen, spun at 225, 000×g for 45 mins. and treated with dextran-coated charcoal. One hundred 1 µl of the cytosol solution, containing 3H-A-AR complexes, was incubated for 6 hrs. with 100 µl of the purified anti-androgen receptor monoclonal antibody, AN1-6, (20× as concentrated as the tissue culture media). Sucrose gradient centrifugation was performed by centrifugation at 257,000×g for 16 hrs. at 4° C. on a 3.8 ml, linear 5–20% (w/v) sucrose gradient containing 20 mM Tris-HCl, pH 7.5, 1 mM EDTA, 1 mM DTT, 10% (v/v) glycerol, and 0.4M KCl. Gradients were fractionated and numbered from the bottom and 0.2 ml per fraction collected. The results obtained indicated that all three of the monoclonal antibodies, AN1-6, AN1-7, and AN1-15, recognized and effectively bound the radioactively labeled androgen receptor ([$^3$H] AR).

The [$^3$H]AR and other steroid receptor complexes had a sedimendation coefficient of about 4–5 S in the sucrose gradient media containing 0.4M KCl. Anti-AR antibodies do not alter the sedimentation coefficient of 4-5S for [$^3$H] glucocorticoid receptors complexes of rat liver, estrogen receptor complexes of MCF-7 cells, and progesterone receptor complexes of T47D cells, but do shift the sedimentation coefficient of [$^3$H]A-AR complexes of rat ventral prostate from 4 S to 9–12 S or to heavier units. By SDS-polyacrylamide gel electrophoresis analysis it was also found that all major in vitro transcription/translation products of human and rat AR cDNAs were immunoprecipitatable by the anti-AR antibodies.

EXAMPLE 14

Use of AR cDNA and TR2 cDNA as Probes in the Study of Abnormality in Human and Animal Organs and Cancer Cells Patients with metastatic prostatic cancer initially often respond favorably to androgen withdrawal therapy (castration or antiandrogen treatments). Most patients, however, eventually relapse to an androgen-state for which no chemotherapy, which would significantly increase the survival rate, is available. Regardless of the origin of androgen-independent or -insensitive cancer cells, it is important to understand whether the androgen insensitivity or abnormality in the diseased cells are due to qualitative or quantitative changes in (a) the AR or TR2 genes, (b) regulation of their transcription, or translation, or (c) other cellular factors. AR cDNA, TR2 cDNA, or their partial segments can be used as specific probes in these studies.

For the analysis of AR or TR2 genes, high molecular weight genomic DNA isolated from target organs, tumors, and cultured cells can be used in identifying and characterizing AR genes. Different restriction endonucleases can be used to cleave DNA. The fragments can be analyzed by Southern analysis (agarose electrophoresis, transfer to nitrocellulose and hybridization with AR cDNA probes). After identification, selected fragments can be cloned and sequenced. It is also possible to use appropriate oligonucleotide fragments of AR or TR2 cDNA as primers to amplify genomic DNA isolated from normal and abnormal organs or cells by specific DNA polymerases. The amplified genomic DNA can then be analyzed to identify sequence abnormality using the polymerase chain reaction (PCR) assay. Saiki, et al., Science, 230, 1350 (1985). See also, Mullis, K. B., U.S. Pat. No. 4,683,202; Jul. 28, 1987; and Mullis, K. B., U.S. Pat. No. 4,683,195; Jul. 28, 1987. For the analysis of mRNA for ARs or related proteins, dot hybridization and Northern hybridization analysis could be used to characterize mRNA and AR or receptor-like molecules quantitatively and qualitatively. From these studies valuable information about the number of different forms of AR genes and their expression in androgen insensitive and sensitive tumor cells can be obtained.

DNAs and RNAs obtained from androgen sensitive and insensitive tumors and from cell lines from rats and humans with testicular feminization syndromes have been analyzed by the above methods. Preliminary studies indicated that abnormality in androgen responses may be due to sequence deletion/mutation in genes for ARs.

EXAMPLE 15

Development of Transgenic Animals

Transgenic techniques have been employed for expression of exogenous DNA. It may therefore be possible to confer androgen sensitivity to animals with androgen receptor defects. For example, androgen insensitive animals, such as testicular feminized mice or rats, are known to have defective AR genes or defective AR itself. If DNA containing a normal AR gene is injected into fertilized mouse embryos, the transgenic mice may carry and express the gene and produce a functional AR necessary for androgen responses. For micro-injection, it is necessary to use AR genes containing DNA that can be expressed in the insensitive animals.

A number of genomic receptor clones from human X-chromosome libraries and rat genomic DNA libraries have been obtained and analyzed for their structures. Clones containing AR sequences will be characterized by endonuclease mapping, by Southern hybridization and by S1-nuclease mapping. The 5' and 3' untranslated regions thus identified will aid in determining the minimal size of the DNA that would be required for tissue specific expression of the AR coding region.

Partial sequence analysis of the 5' and 3' regions would locate the minimal region that represents the promoter and the polyadenylation region. Approximately 2 to 5 kb of upstream un-translated region and 0.5 to 1 kb of sequences downstream from the poly(A) site may be fused to the cDNA clone (minimal-gene) and injected into embryos of mice. Transgenic mice would be identified by analysis of their tail DNA using mini-gene specific probe(s).

Normally only some of the transgenic mouse lines can express their transgenes. Transgenes may be inactive because of the presence of inhibitory sequences, integration of the exogenous gene into a transcriptionally inactive chromosomal location, or the juxtaposition of the transgene and an endogenous enhancer. In addition, androgen insensitivity may be due to various other factors and not due to abnormality in the AR gene or its expression.

The foregoing illustrative examples relate to the isolation of human and rat cDNAs encoding DNA binding proteins including androgen receptor and TR-2 and more particularly describe the transcription of the corresponding cDNAs and translation of the corresponding mRNAs in cell-free systems. While the present invention has been described in terms of specific methods and compositions, it is understood that variations and modifications will occur to those skilled in the art upon consideration of the present invention.

Accordingly it is intended in the appended claims to cover all such equivalent variations which come within the scope of the invention as claimed.

What is claimed is:

1. An isolated and purified DNA sequence encoding human androgen receptor and as set forth in FIG. 3.

2. An isolated and purified DNA sequence encoding human TR2-5 and as set forth in FIG. 4.

3. An isolated and purified DNA sequence encoding human TR2-7 and as set forth in FIG. 4.

4. An isolated and purified DNA sequence encoding human TR2-9 and as set forth in FIG. 5.

5. An isolated and purified DNA sequence encoding human TR2-11 and as set forth in FIG. 6.

6. A prokaryotic or eukaryotic host cell transformed or transfected with a DNA sequence according to any one of claims 1 to 5.

7. A prokaryotic transformed host cell according to claim 6 which is an E. coli DH5α cell designated as, and corresponding to A.T.C.C. Deposit Number: EC-hAR 3600, A.T.C.C. No. 67879; EC-TR2-5, A.T.C.C. No. 67877; EC-TR2-7, A.T.C.C. No. 67876; or EC-TR2-11, A.T.C.C. No. 68173.

8. A viral or circular DNA plasmid comprising a DNA sequence according to any one of claims 1 to 5.

9. A viral or circular DNA plasmid according to claim 8 further comprising an expression control sequence operatively associated with said DNA sequence.

* * * * *